United States Patent [19]

Baker et al.

US005135753A

[11] Patent Number: 5,135,753
[45] Date of Patent: Aug. 4, 1992

[54] METHOD AND THERAPEUTIC SYSTEM FOR SMOKING CESSATION

[75] Inventors: R. W. Baker, Palo Alto, Calif.; Gian C. Santus, Milan, Italy; S. Vintilla-Friedman, Cupertino, Calif.

[73] Assignee: Pharmetrix Corporation, Menlo Park, Calif.

[21] Appl. No.: 669,116

[22] Filed: Mar. 12, 1991

[51] Int. Cl.⁵ .............. A61F 13/02; A61K 9/70; A61K 31/465; A61L 15/16
[52] U.S. Cl. .............. 424/435; 424/434; 424/443; 424/447; 424/448; 424/449; 514/343; 514/813
[58] Field of Search .......... 424/434, 435, 443, 447, 424/448, 449; 514/343, 813

[56] References Cited

U.S. PATENT DOCUMENTS

| | | | |
|---|---|---|---|
| 3,639,607 | 2/1972 | Phillips | 514/813 |
| 3,870,794 | 3/1975 | Hutchinson et al. | 514/343 |
| 4,597,961 | 7/1986 | Etscorn | 514/813 |
| 4,908,213 | 3/1990 | Govil et al. | 424/447 |
| 4,946,853 | 8/1990 | Bannon et al. | 514/813 |
| 5,016,652 | 5/1991 | Rose et al. | 424/447 |
| 5,021,457 | 6/1991 | Akin et al. | 514/813 |

FOREIGN PATENT DOCUMENTS 3241437  5/1984  Fed. Rep. of Germany.

OTHER PUBLICATIONS

"Transdermal Administration of Nicotine", Rose et al., Drug and Alcohol Dependence, 13 (1984) 209-213.

*Primary Examiner*—Thurman K. Page
*Assistant Examiner*—Carlos Azpuru
*Attorney, Agent, or Firm*—Anthony J. Castro

[57] ABSTRACT

A method for smoking cessation therapy is described that utilizes transdermal nicotine delivery for obtaining base-line coupled with buccal administration of nicotine to satisfy transient craving.

17 Claims, 10 Drawing Sheets

METHOD AND THERAPEUTIC SYSTEM FOR SMOKING CESSATION

FIELD OF THE INVENTION

This invention pertains to methods and therapeutic systems for smoking cessation. More particularly, this invention is directed to methods of smoking cessation therapy that consist of transdermal administration of nicotine, and that also consist of buccal administration of nicotine lozenges to provide additional periodic doses of nicotine to satisfy cravings for nicotine in persons who are attempting to quit smoking.

BACKGROUND OF THE INVENTION

Nicotine replacement therapy as an aid to quitting smoking has been practical for a large number of smokers ever since nicotine chewing gum (nicotine polacrilex) became available commercially. Nicotine gum is actually an ion-exchange resin that releases nicotine slowly when the patient chews, and the nicotine present in the mouth is delivered directly to the systemic circulation by buccal absorption. Nicotine gum, however, may be difficult to tolerate as a long-term treatment. The usefulness of nicotine gum formulations are limited because they taste bad, cannot be used effectively by denture wearers, and may lead to mouth ulcers and heartburn. Other difficulties associated with oral administration of nicotine include stomach upsets, nausea, rapid nicotine degradation, and irregular and unpredictable blood plasma levels. In addition, the success of nicotine gum in maintaining even irregular blood levels depends entirely on the patient following a prescribed chewing regime. This regime is extremely inconvenient, particularly for users who need fairly heavy doses.

Another means of nicotine replacement that is commerically available is transdermal administration of nicotine. For some time now, transdermal delivery of nicotine has been known to be a means of administering nicotine for smoking cessation therapy that could avoid the health hazards, adverse effects, and inconvenience of other means of nicotine administration, particularly nicotine gum. Delivery of drugs by the transdermal route has been known to be theoretically possible for many years. The earliest transdermal patches were medicated bandages, usually with the drug mixed into the adhesive, designed to bring a known quantity of drug to a known area of skin for a known time. Such devices do not control the rate at which the drug is released. Controlled release transdermal patches rely for their effect on delivery of a known flux of drug to the skin for a prolonged period of time, measured in hours, days, or weeks. Two mechanisms are typically used to control the drug flux from the patch: either the drug is contained within a drug reservoir, separated from the skin of the wearer by a synthetic membrane, through which the drug diffuses; or the drug is held dissolved or suspended in a polymer matrix, through which the drug diffuses to the skin. Patches incorporating a reservoir and membrane will deliver a steady drug flux across the membrane as long as excess undissolved drug remains in the reservoir; matrix or monolithic devices are typically characterized by a falling drug flux with time, as the matrix layers closer to the skin are depleted of drug. To date limited commercial exploitation of the transdermal administration route has been achieved, because of the many practical problems to be overcome with real systems. The skin is an effective barrier against the majority of drugs. Unless the delivery device is made unacceptably large, or the natural skin permeation rate of the drug is increased, then the drug flux across the skin is inadequate for useful therapy. Thus although in theory any drug might be delivered by this route, serious investigation of candidate drugs has been limited to a few where there are strong indications for transdermal use, namely: small molecular size; short half-life, rapid metabolism by the liver; rapid degradation in the GI tract; other problems with oral administration; high in vivo skin permeability; and high potency, i.e. small effective therapeutic dose. Despite active work in the field since at least 1970, at present commercial patches are available for transdermal delivery of only seven drugs: nitroglycerin, isosorbide dinitrate, scopolamine, clonidine, estradiol, fentanyl, and nicotine.

The concept of applying the teachings of transdermal drug therapy to the delivery of nicotine has been described in the literature, and particularly in U.S. Pat. No. 4,839,174 and U.S. Pat. No. 4,943,435, herein incorporated by reference. Nicotine is a suitable candidate for transdermal therapy because it is volatile, highly lipid soluble, and permeates the skin easily. It is, however, a reactive liquid and a strong solvent. Therefore, transdermal nicotine systems must be made of materials that are compatible with nicotine and can release nicotine at a safe, useful flux.

In addition, these systems should be designed to exploit the benefits of controlled release transdermal therapy. In general, one of the recognized advantages of transdermal therapy as opposed to other drug administration techniques is the simplicity of the dosing regime. A patient using a transdermal patch is less likely to encounter compliance problems than one who is required to subject himself to percutaneous infusion or injection, to swallow pills, or to chew gum two or three times a day, for example. Also, a transdermal patch that has to be changed regularly once a day or once a week, for example, is preferred over one that has to be replaced several times a day, twice a week, or on an irregular schedule. Another major advantage of continuous transdermal delivery is that the blood plasma levels of the delivered agent remain relatively steady. In this way, the periodic fluctuations between plasma levels above the safe threshold and below the efficacy threshold that are often seen with oral tablets or injections are eliminated, as are the "highs" associated with addictive substances. Yet another advantage of a transdermal nicotine system relates to the clinical properties of nicotine, specifically skin irritation and toxicity. Nicotine is a known skin irritant, and a patch that exposes the skin to raw nicotine for any length of time is unacceptable. More importantly, nicotine is a very toxic substance. The lethal unit dose for an average adult is about 60 mg; one cigarette delivers about 1 mg of nicotine. Therefore, a patch that is to be effective for 12 or 24 hours may contain 30 to 60 mg of nicotine, which is a potentially lethal dose. A patient may be exposed to such a lethal dose if the patch is tampered with or ingested by a child, for example. Thus safety is a major concern, and a system that contains a high nicotine load must also be able to control release of that load in such a way that an individual using the patch on his skin is never exposed to a toxic dose. In addition, opportunities for accidental or deliberate misuse must be minimized if possible.

The primary use of transdermal nicotine systems to date has been for smoking cessation therapy. A study by Rose, J. E. et al., in *Clin. Pharmacol. Ther.* 1985, 38, 450-456, demonstrated that systemic delivery of nicotine in pharmacologically useful amounts was feasible by the transdermal route. Studies using human cadaver skin in vitro are likewise consistent with this finding. Typical permeabilities during the first day of patch use are on the order of 0.1 mg/cm$^2$.h, increasing to 0.4 mg/cm$^2$.h and more at later times. Systemic absorption of 20 mg of nicotine (approximately equivalent to smoking one pack of cigarettes) per day would then be theoretically achievable with a dermal administration area of about 10 cm$^2$. This surface area is well within the range of appropriate sizes for transdermal delivery systems. In addition, human clinical studies by Dubois, J. P. et al. in *Meth. and Find. Exp. Clin. Pharmacol.* 1989, 11, 187-195, for example, have demonstrated that application of transdermal nicotine systems results in nicotine blood levels on the order of 10-20 ng/mL, which is comparable to the minimum nicotine blood levels of moderately heavy cigarette smokers. Application of patches for 16 to 24 hours resulted in relatively constant blood levels in this range, indicating that the systems are useful for reliable long-term delivery of nicotine.

Several groups of investigators have described clinical studies that investigated efficacy and safety of transdermal nicotine systems for smoking cessation. Abelin, T. et al. reported on the results of a double-blind study in *The Lancet* 1989, 1, 7-10. They determined that long-term use of a transdermal nicotine patch significantly increased the quit rate in cigarette smokers. The results of this study showed that the number of abstainers in the transdermal nicotine group after one, two, and three months of treatment was significantly greater compared to the placebo group. In another study reported by Mulligan, S. C. et al. in *Clin. Pharmacol. Ther.* 1990, 47, 331-337, the use of a transdermal nicotine patch in a 6-week placebo-controlled double-blind study resulted in a significant degree of smoking cessation. Finally, a report by Rose, J. E. et al. in *Clin. Pharmacol. Ther.* 1990, 47, 323-330 of a randomized double-blind trial indicates that certain smoking withdrawal symptoms were relieved by use of a transdermal nicotine system.

Of the many smoking withdrawal symptoms, however, craving for cigarettes is one of the most difficult to alleviate. As described in Steuer, J. D. and Wewers, M. E. in *Oncology Nursing Forum* 1989, 16, 193-198, cigarette craving is one of the most consistent, most severe, and earliest withdrawal symptoms experienced by those attempting to quit smoking. Some reports suggest that craving peaks over the first 24 to 72 hours of abstinence and then declines, although craving has been reported after five years of abstinence. Research is focusing on the factors that precipitate craving in an attempt to better understand and deal with the problem of relapse. Some investigators believe that certain smokers are much more likely than others to experience craving symptoms, especially when trying to quit smoking. Based on literature reports and his own investigations, Harrington (in *Br. J. Soc. Clin. Psychol.* 1978, 17, 363-371) reported that smokers can be separated by craving vs. noncraving status, and that these separate populations have different responses to smoking cessation therapy. (In his study, treatment consisted of various behavioral strategies, and nicotine replacement was not used). In particular, abstinence during treatment and success at the end of treatment were significantly related to being a noncraver.

With regard to nicotine replacement as a therapy for smoking cessation, some evidence indicates that low consistent blood levels of nicotine (as provided by transdermal nicotine, and to a lesser extent by nicotine gum) relieve some of the symptoms of nicotine withdrawal, but craving symptoms may not be among these (see Russell, M. A. H. in *Nicotine Replacement: a Critical Evaluation*; Pomerleau, O. F. and Pomerleau, C. S., Eds.; Alan R. Liss, Inc.: New York, 1988; pp 63-94). In contrast, cigarette smoking provides a initial sharp rise in blood level, which is missing in these nicotine replacement therapies. The blood level peak produced by cigarettes is both higher (between 30-40 ng/mL) and sharper (this peak is attained within 10 minutes) than the steadier levels obtained from gum or a transdermal system. Russell states that the optimal steady-state blood level for nicotine replacement is between 10-15 ng/mL, but that quick-rise effects are probably necessary for more complete relief from craving in the early stages of cigarette withdrawal. His investigations have indicated that a rise in nicotine blood level of at least 10 ng/mL in 10 minutes is required to obtain postsynaptic effects at nicotinic cholinergic receptors in the CNS and at autonomic ganglia. These postsynaptic effects may be responsible for drug-like "high" feelings such as light-headedness or dizziness experienced by cigarette smokers.

No other commercially available products for nicotine replacement in smoking cessation therapy have specifically addressed the issue of satisfying craving for nicotine. Instead, as mentioned above, they have generally been targeted towards providing a stable baseline level of nicotine in the blood. As described above, nicotine gum is one of the commercially available sources of nicotine for replacement therapy, and indeed is currently the most popular. Nevertheless, Russell (in *Nicotine Replacement: a Critical Evaluation*; Pomerleau, O. F. and Pomerleau, C. S., Eds.; Alan R. Liss, Inc.: New York, 1988; pg. 68) has stated that, compared with cigarette smoking, nicotine gum is a slow and inefficient source of nicotine. Nicotine gum cannot mimic the rapid peaks in the nicotine concentrations of mixed venous blood, or the transient high-nicotine post-inhalation boli in arterial blood, that are characteristic of cigarette smoking. In addition, during ad libitum clinical or experimental use, the 2-mg gum produces steady-state blood nicotine levels that average around one third of the blood level peaks obtained from cigarette smoking. Transdermal nicotine systems can be designed to provide higher steady-state blood levels of nicotine, but are similarly unable to provide blood level peaks or to provide a rapid increase in blood level. Thus both nicotine gum and transdermal nicotine compete with each in other as products providing steady-state nicotine blood levels, but do not satisfy craving symptoms for cigarettes in some smokers.

Other nicotine replacement products that are on the market or have been proposed in the literature have not been of serious interest in smoking cessation therapy, because of problems related to their use, and also because of limited ability to satisfy craving for cigarettes. Nicotine vapor has been delivered to patients in aerosol form, similar to the inhaler technology used to supply bronchial asthma medications, and in a "smokeless cigarette" such as that marketed by Advanced Tobacco Products under the trade name Favor®. Some data indicate, however, that these modes of nicotine delivery do not result in significant nicotine blood levels in patients after use. In addition, inhalation of these nicotine vapor products may be too irritating to the mucosa to be tolerable by patients. Another smokeless version of nicotine delivered to the buccal mucosa is provided by chewing tobacco, oral snuff, or tobacco sachets. Tobacco sachets, which are especially popular in Scandinavia and the U.S., contain ground tobacco in packets that are sucked or held in the mouth. However, as shown in FIG. 1 (from Russell, M. A. H., Jarvis, M. J., et al. *Lancet* 1985, 2, 1370), use of tobacco sachets results in nicotine blood levels that are more comparable to those resulting from nicotine gum use than from those resulting from cigarette smoking; i.e. they require approximately 30 minutes of use to attain the maximum level of approximately 12 ng/mL, which is less than half of the peak value from smoking one cigarette. One possible reason that nicotine from tobacco sachets is absorbed so slowly is that nicotine is released slowly into the mouth, as with nicotine gum; another may be that a significant proportion of the nicotine is swallowed, and therefore subject to the first pass effect of the stomach and liver. In any case, these oral delivery forms may be useful for producing low, steady-state nicotine blood levels, but they do not provide the peak levels needed to satisfy craving.

One U.S. patent describes a combination of two of these modes of nicotine delivery for smoking cessation therapy. U.S. Pat. No. 4,920,989 describes the use of transdermal nicotine systems to provide steady release of nicotine to the patient, combined with the use of a nicotine-containing aerosol spray for oral delivery. The aerosol spray is used periodically in order to provide the patient with sensations in the respiratory tract, and periodic peak blood levels of nicotine, similar to those obtained from cigarette smoke. As mentioned above, however, some reports in the literature suggest that delivery of nicotine by vapor inhalation does not result in significant nicotine blood levels in patients after use, and that inhalation of these nicotine vapor products may be too irritating to the mucosa to be tolerable by patients. In addition, inhaler devices for delivery of aerosol drug products are a much more cumbersome and less discrete dosage form than tablets or skin patches, and some patients are therefore reluctant to use them due to inconvenience and embarrassment. Finally, it is questionable whether this combination mode of therapy would satisfy cravings for cigarettes, because of the lack of proof that inhaled nicotine vapor is useful in providing peak blood levels of nicotine.

The present invention discloses the use of transdermal nicotine systems to provide steady release of nicotine to the patient, plus the period use of nicotine lozenges to provide rapid delivery of nicotine to the buccal mucosa, resulting in transient blood level peaks that mimic the effects of cigarette smoking. The literature describes other capsules, tablets and lozenges for oral delivery of nicotine, but these are designed to be the sole form of nicotine replacement for a patient trying to quit smoking. For example, WO 8803803 discloses a chewable capsule filled with a liquid containing 0.1-10.0 mg of nicotine, together with additives for improving flavor and dispersion. The capsules are provided in a variety of pH values to allow the patient a choice of nicotine absorption rate, and are especially intended as an aid to quitting smoking. Another nicotine capsule formulation is disclosed by M. E. Jarvik et al. (in *Clin. Pharm. Ther.* 1970, 11, 574-576) for ingestion as a smoking cessation aid. These capsules, however, were apparently swallowed whole by the subjects, according to the theory that intestinal absorption of nicotine could produce significant blood levels, intestinal absorption should be very low due to the intense first pass effect by oral route and consequent metabolism of nicotine in the GI tract. The study showed a small but significant decrease in the number of cigarettes smoked by subjects, but no quantitative measurements of nicotine blood levels were obtained.

The literature also describes different designs of tablets for delivering nicotine to the mouth and digestive system. BE 899037 discloses a tablet containing 0.1 to 5 mg nicotine as a base or water-soluble acid salt as an aid for quitting smoking. The tablet is intended to be sucked in the mouth so as to provide very low doses of nicotine to the patient. Wesnes and Warburton (in *Psychopharmacology* 1984, 82, 147-150; and *Psychopharmacology* 1986, 89, 55-59) discuss the use of nicotine tablets in experiments examining the effects of nicotine on learning and information processing. In the first experiment nicotine was added to dextrose tablets with a drop of tabasco sauce added to disguise the taste of nicotine. In the second experiment nicotine was added to magnesium hydroxide tablets, under the theory that an alkaline environment in the mouth would enhance buccal absorption. Again, tabasco sauce was added to the tablets to mask the taste of nicotine in both active and placebo tablets. The subjects were instructed to hold the tablets for 5 minutes in the mouth before swallowing, in order to maximize contact with the buccal mucosa.

Shaw (for example in GB 2142822 and U.S. Pat. No. 4,806,356) describes a nicotine lozenge prepared from a mixture of inert filler material, a binder, and either pure nicotine or a nicotine-containing substance by cold compression. The lozenges are intended to be held in the mouth as the dissolve slowly and release nicotine gradually in the buccal cavity, as a nicotine replacement for satisfying a craving for nicotine. It will be noted, however, that if the nicotine is intended to be released slowly into the mouth, then the corresponding blood level of nicotine is likely to rise slowly, instead of peaking rapidly as with cigarette smoking.

The present invention describes the use of transdermal nicotine systems to provide steady release of nicotine to the patient, resulting in consistent low nicotine blood levels. It also describes the periodic use of nicotine lozenges in conjunction with the transdermal therapy. The nicotine lozenges are designed to be held in the patient's mouth and sucked, and to rapidly release nicotine into the buccal cavity, resulting in transient blood level peaks that mimic the effects of cigarete smoking. Thus the patient is provided with a consistent transdermal dose of nicotine, plus transient oral doses that aid in satisfying cravings for cigarettes. This method of therapy more closely mimics the nicotine blood levels achieved by consistent smoking, and will provide greater protection against relapse than other nicotine replacement therapies for people who are trying to quit smoking.

SUMMARY OF THE INVENTION

The present invention consists of use of transdermal nicotine patches together with nicotine lozenges as a method of smoking cessation therapy.

The transdermal patch used is one that can hold and deliver sufficient nicotine to be effective for a period of 12 hours or more, preferably 24 hours, for smoking cessation therapy. The patch therefore provides the major benefits of controlled-release drug delivery systems, such as steady blood plasma levels of nicotine, convenience, patient acceptance, reduced side effects, and so on. The patch may take the form of a reservoir system, in which the depot of nicotine is separated from the skin by a nonporous polymeric membrane, through which the nicotine diffuses at a controlled rate. The patch may also be in the form of a monolithic matrix, consisting of a single phase solution or mixture of nicotine in a polymeric material, and wherein the nicotine is released by diffusion through the solution. A third possible embodiment involves a combined system from which nicotine is released by a combination of diffusion through a polymeric solution, and diffusion across a polymeric membrane. Embodiments employing a monolith of nicotine in a polymeric carrier are particularly preferred.

The patches of the present invention comprise a nicotine depot layer capable of holding a sufficient quantity of nicotine for smoking cessation therapy during a period of at least 12 to 24 hours. One side of this layer is in contact with an occlusive backing. The backing is nicotine-impermeable and prevents loss of nicotine by evaporation to the surrounding environment during use. The other side of the layer faces the skin of the user. Depending on the particular embodiment, this layer may, but need not, be separated from direct contact with the skin by means of a polymeric membrane, a layer of medical tape, or a continuous or discontinuous adhesive layer. The third element of the patch is a means for controlling the rate of diffusion of nicotine from the patch. This means may take the form of a polymeric membrane, preferably nonporous, a polymeric solution in which the nicotine is dissolved or dispersed, or a combination of these. The patches of the invention are normally attached adhesively to the skin of the user, although other attachment means that would hold the patch closely against the skin could be contemplated by the art.

The nicotine lozenge used is one that is intended to be held and sucked in the mouth, and that delivers nicotine rapidly to the buccal cavity. Delivery to the patient through the buccal mucosa is rapid and also bypasses the first pass effect of the stomach and liver. The lozenge contains fairly low doses of nicotine, preferably less than 5 mg, and most preferably from 0.5 to 2.0 mg, to avoid accidental overdosage by swallowing the lozenge intact. In addition, high doses are not required because the purpose of the nicotine lozenge is to provide a transient blood level peak of nicotine. The lozenge preferably is a buffered formulation in order to aid in buccal absorption of nicotine. A preferred formulation is at a pH of 6-11, and more preferably at a pH of 7-9. The lozenge is used without holding any other substance, such as food or beverage, in the mouth, and it is particularly important that acidic substances or beverages such as fruits, coffee, tea, or fruit juices are not consumed immediately preceding or concurrently with the nicotine lozenge, in order to insure that a basic environment is maintained within the mouth.

OBJECTS OF THE INVENTION

It is an object of the present invention to provide devices and methods for smoking cessation therapy.

It is a further object of the present invention to provide devices and methods for smoking cessation therapy by transdermal administration of nicotine combined with buccal administration of nicotine in a lozenge form.

It is a further object of the present invention to provide devices and methods for smoking cessation therapy that avoid unpleasant side effects of nicotine administration.

It is a further object of the present invention to provide devices and methods for smoking cessation therapy by transdermal administration of nicotine and buccal administration of nicotine lozenges that avoid or minimize skin irritation.

It is a further object of the present invention to provide devices and methods for smoking cessation therapy by transdermal administration of nicotine and buccal administration of nicotine lozenges that avoid or minimize overdose risks.

It is a further object of the present invention to provide devices and methods for smoking cessation therapy by transdermal administration of nicotine that can maintain steady levels of nicotine in the patient's blood plasma for prolonged periods, and that can also, by buccal administration of nicotine lozenges, provide additional peak levels of nicotine in the patient's blood plasma on demand to satisfy cravings for nicotine in people who are attempting to quit smoking.

Further objects and advantages of the invention will be apparent from the description of the invention to those skilled in the art.

DETAILED DESCRIPTION OF THE INVENTION

"Transdermal system" as used herein means any system or device that is attached to the skin of a patient and is used to deliver a drug through the intact skin and into the patient's body.

"Buccal Administration" as used herein means any system or device for oral administration of a drug to a patient, that is held in the mouth and is used to deliver a drug through the buccal mucosa and into the patient's body. This term includes, but is not limited to, lozenges, capsules and tablets.

"Nicotine" as used herein means pure nicotine, nicotine free base, or any salt or compound thereof.

"Prolonged period" as used herein means about 12 hours or more.

"Monolith" as used herein means a single-phase combination of nicotine and a polymeric carrier.

The present invention consists of transdermal systems and lozenges used together to deliver nicotine to a patient for smoking cessation therapy, and methods of using transdermal systems and lozenges for this purpose. The invention consists of any form of transdermal system and lozenge used together for this purpose, and all methods of use of these systems for this purpose, including but not limited to the embodiments and methods described below.

Figure 1:
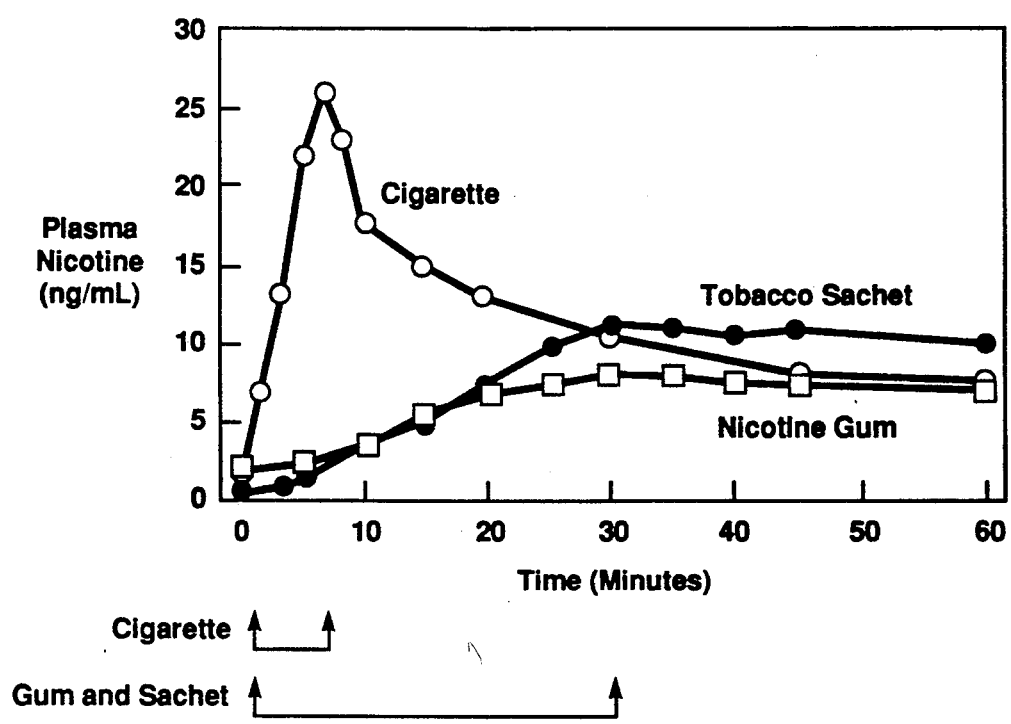
FIG. 1 is a graph of average nicotine plasma levels resulting from use of cigarettes, tobacco sachets, or nicotine gum.
Figure 2:
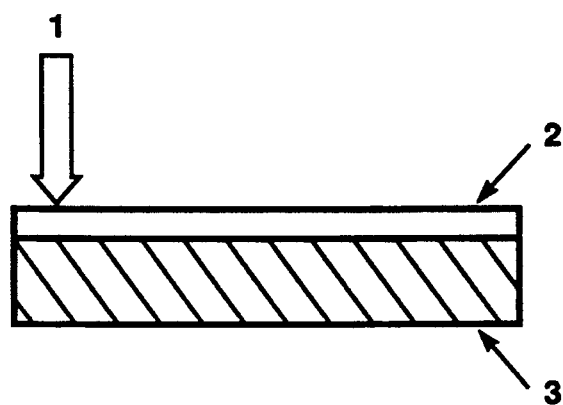
FIG. 2 shows an embodiment of the invention including an impermeable backing and a monolithic nicotine-containing matrix.

A basic embodiment of the transdermal nicotine system described in the present invention is shown in FIG. 2. Referring now to this figure, the nicotine dispensing patch, 1, comprises an impermeable backing layer, 2, and a monolithic matrix layer, 3, which both serves as a depot for the nicotine, and controls the rate at which it diffuses to the skin.

The impermeable backing layer, 2, defines the non-skin facing, or skin distal, side of the patch in use. The functions of the backing layer are to provide an occlusive layer that prevents loss of nicotine to the environment, and to protect the patch. The material chosen should therefore be nicotine resistant, and should exhibit minimal nicotine permeability. The backing layer should be opaque, because nicotine degrades when exposed to ultraviolet light. Ideally, the backing material should be capable of forming a support onto which the nicotine-containing matrix can be cast, and to which it will bond securely. A preferred material is polyester or aluminized polyester. Polyester has a nicotine permeability less than 0.2 $\mu$g.100 $\mu$m/cm$^2$.h. Preferred backings are polyester medical films, available for example from 3M Corporation as Scotchpak® 1005 or 1109. While applicants believe that there are relatively few materials that are really sufficiently impermeable to nicotine to retain the nicotine load adequately during storage or use, other low permeability materials that might be tried include, for example, metal foil, metallized polyfoils, composite foils or films containing polyester, Teflon (polytetrafluoroethylene) type materials, or equivalents thereof that could perform the same function. As an alternative to casting the matrix directly on the backing, the polymer matrix may be cast separately and later stuck to the backing layer.

The nicotine monolith layer, 3, comprises nicotine finely dispersed, or preferably dissolved, in a polymer matrix. The monolith layer may be prepared as follows. First a solution of the polymer matrix material is made. Nicotine, preferably liquid, is then added to the polymer solution, and the mixture is homogenized. The percentage by weight of nicotine in the solution may be varied according to the desired loading of the finished monolith. The upper limit on the amount of nicotine that can be incorporated is determined by the stability of the solution. Above about 50 weight percent nicotine, the monolith becomes a solution of the polymer in nicotine, rather than nicotine in the polymer, and depending on the polymer used, a point is reached where it is no longer possible to cast a stable film, because the solution remains in gel form or fluid form after casting. The monolith solution may be poured into a mold or cast alone or on the desired backing material. The casting is then covered and left for the solvent to evaporate at room temperature. After solvent evaporation, the monolith takes the form of a polymer film typically having a thickness in the range of about 50 to 800 $\mu$m. It will be appreciated that for a given desired total nicotine load, the percentage loading may be varied by varying the monolith thickness. In embodiments where the monolith is formed apart from the backing layer, a backing may be provided, for example, by attaching a layer of single-sided occlusive medical adhesive tape to one face of the cast film. The total nicotine content of the monolith will be sufficient to provide one day's supply. This amount depends on the user's need for nicotine. [As a rough guide, a delivered load somewhere between 5 mg and 50 mg may be appropriate in smoking cessation therapy.] It is probably not desirable to go above about 50 mg delivered nicotine content, because of the toxicity hazard, although in theory patches of this type with a bigger load can be made. Also, the amount of nicotine in the patch as made may exceed the delivered load because, as the patch becomes exhausted, there will be an insufficient concentration gradient to remove all the nicotine. Consequently, the activity of the patch may fall below useful levels.

A feature of these monolith embodiments is that they provide a solution to the problems of skin irritation and potential toxicity. The activity of nicotine on the skin will be representative of the concentration of nicotine in the monolith. Thus a monolith with a nicotine content of 30 wt % will exhibit the activity of a 30% solution, rather than pure nicotine, on the skin, with consequent substantial reduction or elimination of skin irritation. The release mechanism for the nicotine is diffusion under a concentration gradient. Therefore, even if the patch were to be ingested, the nicotine release would be still a gradual process, and the victim would not be exposed to a very large, toxic, or lethal unit dose. Systems where the nicotine is held in an absorbent material, or mixed in with some other liquid or gel, do not have this advantage.

To ensure that a user cannot be exposed to a toxic dose when the patch is used correctly, the in vitro nicotine flux from the patch must stay within certain limits. This is a much more critical issue with nicotine than with most drugs, because nicotine is very skin permeable, very toxic, and very irritating. This can be understood if the average penetration rates of other transdermally administered agents through the skin are compared with nicotine. For example, nitroglycerin has a skin flux of 10–25 µg/cm$^2$.h, scopolamine 2–8 µg/cm$^2$.h, estradiol 0.01–0.03 µg/cm$^2$.h, and clonidine 0.5 µg/cm$^2$.h. The skin flux of nicotine is about 100–300 µg/cm$^2$.h. It should be appreciated that these are very approximate figures. One of the recognized problems in the art is that skin permeabilities can vary 20-fold or more between individuals and between different skin sites on the same individual. Therefore, in the case of nitroglycerin for example, a rare individual having a skin permeability 10 times greater than the average, using a transdermal system with an in vitro flux as great or greater than skin permeability, would be exposed to 100–250 µg/cm$^2$.h of drug. On the other hand, that same individual using a nicotine patch with an area of 10 cm$^2$ and an in vitro release of 2 mg/cm$^2$.h, could absorb 20 mg nicotine per hour, a substantial fraction of the lethal dose. It is thus clear that a patch with a large nicotine load must be able to control release of that load, such that the in vitro flux from the patch does not exceed about 10 times, preferably about 5 times, and more preferably about equals, the average skin permeation rate. Of course, embodiments where the in vitro flux from the patch is less than the skin permeation rate, such that the systemic absorption is controlled primarily by the patch rather than the skin, are acceptable, so long as the systemic nicotine level can be sustained above the necessary minimum level for that individual's needs.

Polyurethanes are a preferred polymer for forming the monolith film, because they have been found to form stable solutions with nicotine, and they exhibit suitable nicotine permeabilities. The polyurethane used may be a polyether, polycarbonate, hydrocarbon or polyester type. Polyether-type polyurethanes are preferred, because in general they are more inert than polyester-types, and thus more appropriate for biomedical use. Polyether-type polyurethanes are typically made by reacting a hydroxyl-terminated polyether oligomer with a diisocyanate according to the reaction:

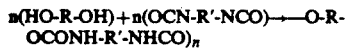

n(HO-R-OH)+n(OCN-R'-NCO)→—O-R-OCONH-R'-NHCO)$_n$ where R is the polyether group. This prepolymer is then further reacted with another diol where R is small, for example, 1,4-butanediol, to yield a thermoplastic, elastomeric polymer, the properties of which can be tailored by adjusting the proportions of polyether and butane diols. Polymers of this type in grades approved for medical use may be purchased from Dow Chemical, Midland, Mich., under the name Pellethane ®. Different hardnesses are available; the softer grades are generally desirable in the present context because they are easier to dissolve and handle. Solvents that may be used to dissolve polyurethane include tetrahydrofuran (THF, T425-4, Fischer Scientific, Springfield, N.J.), dimethylsulfoxide (DMSO), and dimethylformamide (DMF). Tetrahydrofuran is approved for use with medical materials so long as the residue remaining in the material after evaporation does not exceed 1.5 wt %. It is usually desirable to make the concentration of polyurethane in the solvent that has to be evaporated as high as possible, so that the quantity of solvent that has to be evaporated is minimized. Other polymers than polyurethane that can exhibit equivalent monolith forming and nicotine flux characteristics are intended to be within the scope of the present invention. Examples that might be used, depending on the desired nicotine load, film thickness, etc. include methacrylate polymers such as polymethyl methacrylate or polybutyl methacrylate, or ethylene-acrylic acid polymers, or functional equivalents.

Figure 3:
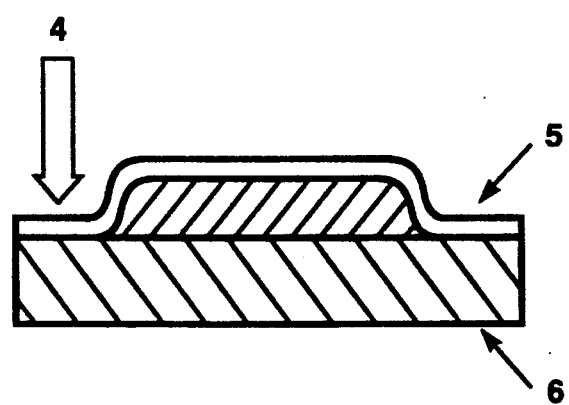
FIG. 3 shows an embodiment of the invention including an impermeable backing, a nicotine depot, and a rate-controlling polymer membrane.

Another embodiment of the invention is shown in FIG. 3. Referring now to this figure, the nicotine dispensing patch, 4, comprises an impermeable backing layer, 2, a nicotine reservoir, 5, and a polymer membrane, 6. The backing layer may be the same as that used for the monolith embodiment described above. The reservoir may take various forms, for example, pure nicotine, nicotine diluted with a liquid or gelled carrier, or nicotine contained within the pores of a microporous matrix. These reservoir systems are distinguished from the monolith embodiments of FIG. 2 in that the function of the reservoir layer is to be a depot for the nicotine and to keep it in good contact with the membrane layer. The reservoir layer does not contribute to any measurable extent to the rate-controlling mechanism. To discourage tampering with the patch, or misuse of the contents, it may be desirable to mix the nicotine with other materials as described in U.S. Pat. No. 4,597,961 to Etscorn, incorporated herein by reference. If the patch is to be loaded with a comparatively small quantity of nicotine, then the nicotine can be conveniently kept in contact with the membrane layer by holding it in the pores of a microporous matrix. Applicants have found that a disk of microporous nylon can be used. The disk also decreases the user's risk of exposure to a high dose of nicotine should the patch become accidentally ruptured. The polymer membrane layer, 6, is the rate-controlling means that regulates the flux of nicotine from the patch to the skin. The criteria for selection of a suitable material are those discussed in the background section above, namely resistance to attack by nicotine, and possession of an appropriate permeability for nicotine. The polymer chosen should also be compatible with the other components, and workable by standard techniques that are used in fabrication of the patch, such as casting or heat sealing. Dense nonporous membranes have a substantial advantage over microporous materials. Microporous membranes release the contents of the patch by pore flow. Thus, in areas of the pores, the skin is exposed to raw nicotine. Also, in the case of a volatile liquid such as nicotine, flow through the pores occurs rapidly, so that the system is quickly exhausted, and the skin is flooded with excess nicotine for the life of the patch. In contrast, diffusion of nicotine through a nonporous film takes place by dissolution of the nicotine in the film, followed by diffusion under a concentration gradient. By selecting materials with suitable permeabilities, and making a membrane of appropriate thickness, it is possible, as taught by applicant, to tailor systems that can release their nicotine load gradually over 12 or 24 hours in a safe, controlled fashion. Furthermore, the solution/diffusion mechanism protects the patient's skin from exposure to excess amounts of raw nicotine. Based on extensive experimentation, applicants believe that preferred membrane polymers are low, medium, or high density commercial polyethylenes. Particularly suitable are the grades obtainable under the trade name Sclairfilm ® from DuPont Canada or those from Consolidated Thermoplastics. The 3M Corporation also manufactures a line of polyethylene membranes faced with adhesive tapes that are very suitable. Other possible membrane materials are polyamides, such as nylon 6,6, or some grades of ethylene vinyl acetate copolymers. Functional equivalents of these are intended to be within the scope of the invention. The membrane layer may be formed by preparing a solution of the chosen polymer in an organic solvent, casting on a glass plate or in a mold, and drying to evaporate the solvent. The thickness of the finished film is tailored to give the desired nicotine flux. In general, membranes used in transdermal patches have thicknesses ranging from about 5 μm to about 200 μm. Alternatively, it may be possible to purchase the membrane already in film form. This type of transdermal patch may be prepared by heat-sealing the backing to the membrane layer around the perimeter of the patch. The nicotine formulation may be added either before or after heat sealing. If the formulation is added before heat sealing, it is convenient to shape the backing so as to form a cavity for retention of the nicotine, or to gel the nicotine. If the formulation is incorporated after heat sealing, the nicotine may be injected into the pouch formed by the heat sealing process, and the injection hole sealed.

As discussed for the monolithic embodiments, the patches of the present invention may frequently be required to hold a total nicotine load that is 50% or more of the lethal dose. It is therefore important that the patches be able to control the nicotine flux to the skin within safe limits at all times. In this regard, reservoir-type embodiments have an advantage over the monolith systems. The advantage is that, so long as undiluted nicotine remains in contact with the reservoir side of the membrane, the nicotine flux through the membrane remains relatively constant over the life of the patch. Monolith-type embodiments, on the other hand, often exhibit a falling flux with time, as the portion of the monolith closer to the skin becomes depleted of drug. As discussed above, these kinds of considerations matter more when dispensing nicotine than with many other substances. Suppose that a transdermal patch, tested in vitro, delivers a substantial fraction of its total drug load during the first few hours, at a flux several times higher than the average skin permeation rate. The in vitro flux then falls off to levels that are well below the average skin permeation rate until the patch is exhausted. When this patch is applied to the user, the skin will be saturated with drug and the drug will pass through the skin at a rate determined by that user's skin permeability. Typically a "depot" of drug will build up in the skin, and the drug will gradually reach the systemic circulation from this depot. Individuals with unusually high skin permeabilities will build up a larger skin depot faster than those with low skin permeabilities. For drugs that are less toxic than nicotine, less irritating to the skin, and/or have much lower skin permiabilities, this "skin depot" phenomenon may be perfectly acceptable, or even preferable, since it tends to balance out the falling flux from the patch. Many transdermal patches currently available exhibit this effect and function satisfactorily in this way. However, for nicotine, the situation is different. A patch that can avoid this high initial drug burst, with consequent skin irritation or risk of overdose, is desirable. Any initial flux from the patch should not exceed a maximum of 2 mg/cm$^2$.h, and more preferably should not exceed 1 mg/cm$^2$.h. Any flux this high should never be sustained fro more than 4-5 hours, and preferably should not be sustained for more than 1-2 hours. Depending on the drug load, the skin permeability of the patient, and the drug flux required, it may be easier to stay within this limit with a reservoir-type patch. The risk of accidental overdose if the patch is damaged or ingested, however, is minimized with monolithic embodiments. There will therefore be circumstances where one or the other type of patch is preferably indicated.

Figure 4:
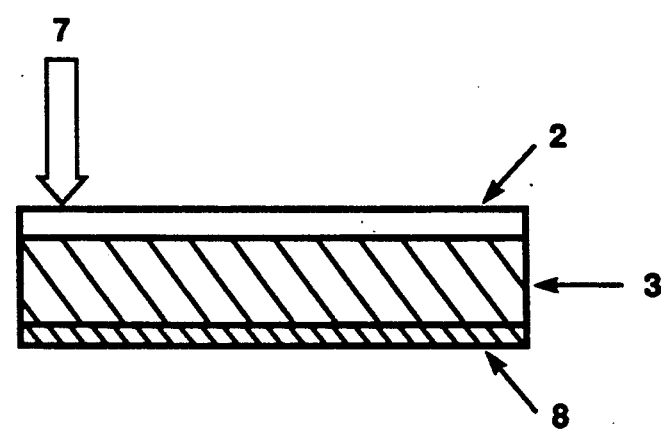
FIG. 4 shows an embodiment of the invention including an impermeable backing, a monolithic nicotine-containing matrix, and a polymer membrane.

As a way to exploit the advantages of both reservoir and monolith systems, applicants believe that a particularly preferred embodiment is shown in FIG. 4. Referring now to this figure, the nicotine dispensing patch, 7, comprises an impermeable backing layer, 2, a monolithic matrix layer, 3, and a polymer membrane layer, 8. The backing and monolith layers are selected and prepared as described for the embodiment of FIG. 2. The membrane layer may be selected and prepared as described for the embodiment of FIG. 2. Alternatively, and preferably, the membrane layer may take the form of a double-sided medical adhesive tape, which may be conveniently be attached to the finished monolith on the skin-facing side. If the tape contains a polymer backbone material that offers resistance to nicotine permeation, then this adhesive layer may have a nicotine permeability of the same order or less than the monolith material, so that the adhesive layer serves as a thin membrane limiting flux of nicotine from the patch. The system functions as a mixed monolith reservoir system, where the nicotine release characteristics depend both on the monolith layer and the membrane polymer. The preferred tapes for use in this way are those with a polyethylene backbone, such as 3M-1509, a 75 μm thick medical tape containing medium density polyethylene, and 3M-1512, a 38 μm thick polyethylene tape, both available from 3M Company. The additional resistance to permeation created by the tape assists in holding the nicotine load in the patch and moderates the initial high drug flux. This embodiment is particularly useful in cases where the percentage nicotine load of the monolith is high, say more than about 30 wt %, or where the total nicotine load is high, say 30 mg or more. Systems with this amount of nicotine are more likely to exhibit a large burst effect on initial application to the patient's skin than those with low nicotine content. The additional resistance of the membrane/tape layer is useful in keeping the initial nicotine flux within therapeutically acceptable levels. Other advantages associated with this embodiment include a nicotine activity representative of the concentration of nicotine in the monolith, so that skin irritation and adhesive degradation are minimized. The risk of an overdose of nicotine is reduced, because the monolith cannot release its nicotine load in a single burst if the patch is damaged or even swallowed.

In use, the patches of the present invention may be held in contact with the patient's skin in a variety of ways, such as by means of a porous or nonporous overlay coated wholly or partly with adhesive, by an adhesive layer between the patch and skin, or by an annulus of adhesive around the periphery of the patch. Of course, the mixed reservoir/monolith embodiments with adhesive medical tapes do not require additional adhesive.

If an adhesive layer is to be included as an integral part of the patch, the adhesive should be nicotine compatible and permit a useful nicotine flux. In addition, the adhesive should satisfy the general criteria for adhesives used for transdermal patches in terms of biocompatibility, ease of application and removal, etc. Suitable adhesives for use in the practice of the invention include pressure-sensitive adhesives approved for medical use. Amine-resistant types are preferred, so that the adhesive will not be attacked by the nicotine. A range of silicone-based amine-resistant medical adhesives is offered by Dow Corning under the trade name BIO PSA. Alternatively, acrylate-type adhesives with amine resistance can be used. The adhesive layer can be cast directly onto the skin-facing side of the membrane or monolith as a thin film. Alternatively, medical adhesive tape, with or without nicotine-flux controlling properties, may be used.

Loss of nicotine from the patch after manufacture should be kept to a minimum. Normally, the skin-facing side of the patch will be covered with a peel strip until the patch is used. As stressed throughout, nicotine is volatile, and retention of the nicotine load within the patch during storage requires that the outer layers are extremely nicotine-resistant and nicotine-impermeable. The peel strip therefore should possess the same properties as the backing layer, and the same materials are preferred.

The patches of the present invention enable smoking cessation therapy to be carried out by application of a transdermal patch. The total amount of nicotine released by the patch during the period of use will vary depending on the user's body size, history of exposure to nicotine, and response to treatment, but will be roughly in the range of 5-50 mg. In general, this dosage will maintain the nicotine blood level at a baseline level of between 5 to 30 ng/mL nicotine, and more preferably between 10-20 ng/mL, which is believed to be the preferred steady-state blood level for optimal therapy in most patients. The amount of nicotine delivered, and the dosing regime used, may vary depending on the patient's age, body size, and severity of smoking habit.

General guidelines for patch design must ensure that the patient is protected at all times from toxic doses of nicotine, and must also ensure that the patient receives a dose of nicotine that will be effective for smoking cessation therapy. The in vitro flux from any individual patch used for the intended therapy should remain below about 800 $\mu g/cm^2.h$, preferably below 600 $\mu g/cm^2.h$, and more preferably below 400 $\mu g/cm^2.h$ during the life of the patch. Staying within these limits ensures that a patient with unusually permeable skin can never receive a toxic dose. The size of the patch will vary according to the amount of nicotine to be delivered. For an average individual, nicotine flux through the skin is about 100-300 $\mu g/cm^2.h$. Therefore, to deliver 25 mg in a 24-hour period, the patch would have a skin-contacting area of about 3-10 $cm^2$. To maximize patient acceptance and compliance, and to minimize any skin irritation, the patch size should not exceed about 25 $cm^2$ maximum skin covering area. With the systems and release characteristics taught by applicant, it should be possible to keep the patch size in the range 1-20 $cm^2$, preferably 2-10 $cm^2$.

The nicotine lozenge of the present invention consists of any lozenge, tablet, or capsule formulation that delivers nicotine to the buccal cavity. The nicotine form that is added or incorporated into the lozenge formulation may be pure nicotine or any compound thereof. The method of manufacture of these lozenges may be any suitable method known in the art, including but not limited to the addition of a nicotine compound to pre-manufactured tablets; cold compression of an inert filler, a binder, and either pure nicotine or a nicotine-containing substance (as described in U.S. Pat. No. 4,806,356, herein incorporated by reference); and encapsulation of nicotine or a nicotine compound. Examples 29-38 present detailed descriptions of several methods of manufacture of nicotine lozenges. Examples 29-36 describe the manufacture of nicotine lozenges intended to be chewed or sucked in the mouth. Of these examples, Examples 30-36 describe manufacture of nicotine lozenges that are buffered so as provide optimal absorption of nicotine by the buccal mucosa. Example 37 describes the manufacture of nicotine sublingual tablets, where the nicotine is mixed with a granulate and then compressed into a tablet. Example 38 describes the manufacture of a soft chewable nicotine gelatine capsule formulation that allows for precise dosing. Another oral formulation that is disclosed in the present invention is one that can be applied with an adhesive, such as the cellulose derivative hydroxypropyl cellulose, to the oral mucosa, for example as described in U.S. Pat. No. 4,940,587. This buccal adhesive formulation, when applied to the buccal mucosa, allows for controlled release of nicotine into the mouth and through the buccal mucosa.

In any formulation used, the lozenge contains fairly low doses of nicotine, preferably less than 5 mg, and most preferably from 0.5 to 2.0 mg, to avoid accidental overdosage by swallowing the lozenge intact. In addition, high doses are not required because the purpose of the nicotine lozenge is to provide a transient blood level peak of nicotine. Use of the lozenge will result in transient nicotine blood level peaks that are at least 5 ng/mL higher, and more preferably at least 10 ng/mL higher, than the consistent nicotine blood level provided by the transdermal nicotine system that is used concurrently. Use of the lozenge will result in this transient nicotine blood level peak from 2 to 30 minutes, and more preferably from 2 to 10 minutes, after the lozenge is placed in the mouth. The lozenge preferably is a buffered formulation in order to aid in buccal absorption of nicotine. A preferred formulation is at a pH of 6.8-11. Preferred buffered formulations will include sodium carbonate, sodium phosphate, calcium carbonate, magnesium hydroxide, magnesium carbonate, aluminum hydroxide, and other substances known to those skilled in the art. The lozenge may contain a candy taste, such as a mint or other flavor, to mask the taste of nicotine. The lozenges may be packaged in such a manner as to aid in maintaining nicotine stability. Preferred packaging methods include strip lamination in a foil-like material such as Barex ®, or packaging in blisters using a teflon-like material such as Aclar ®.

The present invention consists of a method of using transdermal nicotine systems and nicotine lozenges as an aid for smoking cessation. The transdermal systems are applied to the skin in a manner so as to maintain a low and consistent level of nicotine. The length of time that each transdermal patch is used will depend on the patient's age, body size, the patient's tolerance for nicotine, and other factors. The nicotine lozenges of the present invention are used to provide periodic transient blood level peaks of nicotine, as an aid in reducing symptoms of craving of nicotine. The lozenges may be used ad libitum by the patient, in order to alleviate cravings for nicotine as they arise, or they may be used according to a dosage pattern prescribed by a physician. The lozenge is used without holding any other substance, such as food or beverage, in the mouth, and it is particularly important that acidic substances or beverages such as fruits, coffee, tea, or fruit juices are not consumed immediately preceding or concurrently with the nicotine lozenge, in order to insure that a basic environment is maintained within the mouth. The lozenge is preferably held from 2-10 minutes in the mouth as it dissolves completely and releases nicotine into the mouth, and the dissolved nicotine solution is held in the mouth for as long as possible so that the nicotine is absorbed through the buccal mucosa.

The invention is now further illustrated by Examples 1 to 38, which are exemplary but nonlimiting.

Examples 1-5

Monolith Embodiments

EXAMPLE 1

Figure 5:
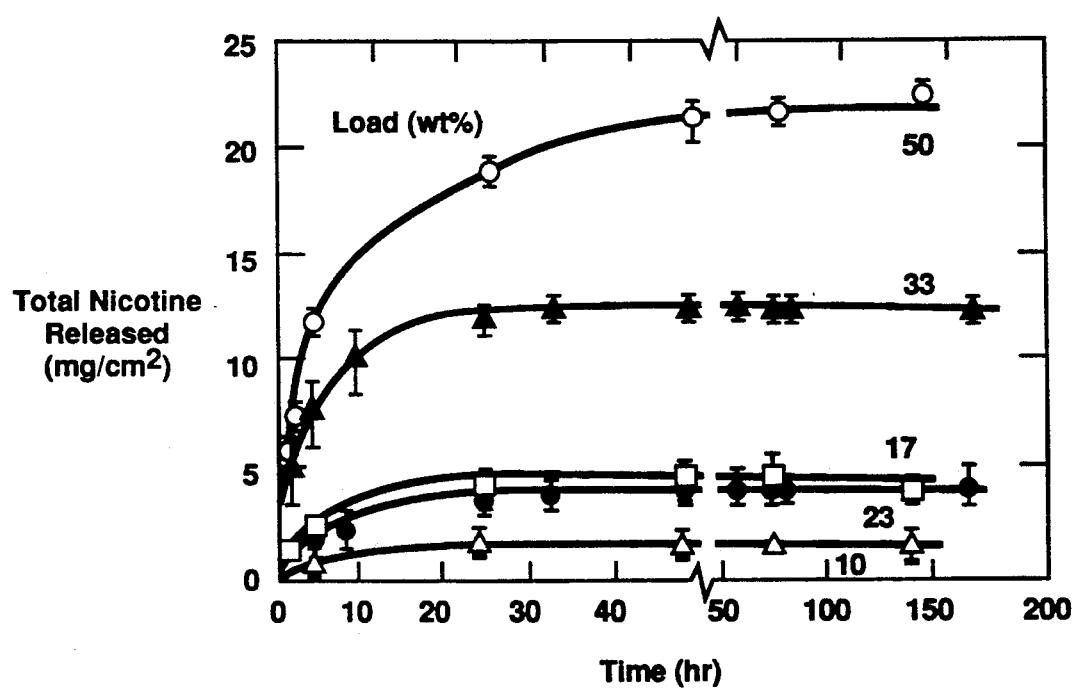
FIG. 5 is a graph of total nicotine release against time for a polyurethane/nicotine monolith.

Monolithic patches were made as follows. A solution of nicotine-loaded Pellethane ® 2363-80AE was made by mixing Pellethane pellets into tetrahydrofuran, adding 10 wt % liquid nicotine, and agitating on a bottle roller for three days. A layer of backing material grade 3M-1005 was spread in a petri dish and covered with the matrix mixture. The petri dish was covered, and the matrix was left for the solvent to evaporate at room temperature. Patches with an area of 3.88 cm² were cut from the finished matrix with a punch, and device release-rate measurements were made as follows. Each test device was suspended in a wire cage in an isotonic saline solution, constantly agitated by a magnetic stirrer, and maintained at 30° C. Periodic saline samples were taken for HPLC analysis using a Novapak C18 column. The results are given by the lowest curve in FIG. 5.

EXAMPLE 2

Monolithic patches were made and tested by the same procedure as described in Example 1, except that the nicotine content of the matrix mixture was 17 wt %. The results of the release tests are given by the second curve in FIG. 5.

EXAMPLE 3

Monolithic patches were made and tested by the same procedure as described in Example 1, except that the nicotine content of the matrix mixture was 23 wt %. The results of the release tests are given by the third curve in FIG. 5.

EXAMPLE 4

Monolithic patches were made and tested by the same procedure as described in Example 1, except that the nicotine content of the matrix mixture was 33 wt %. The results of the release tests are given by the fourth curve in FIG. 5.

EXAMPLE 5

Monolithic patches were made and tested by the same procedure as described in Example 1, except that the nicotine content of the matrix mixture was 50 wt %. The results of the release tests are given by the fifth curve in FIG. 5.

EXAMPLE 6

Membrane Flux Tests

Promising membrane polymers that appeared to be able to withstand nicotine were tested for their nicotine permeability. The experimental procedure in each case was as follows. Samples of the films were mounted in teflon flow-through diffusion cells. Buffered isotonic saline was circulated through the bottom of the cell. Membrane samples were mounted on the bottom of each cell fixed by the threaded neck that also acts as the drug solution reservoir. The exposed area of the membrane was 3.9 cm². The membrane permeability was measured by the rate of permeation of nicotine into the saline solution. The samples were:

Dartek ® F101: nylon 6,6
Sclairfilm ® HD-2-PA: high density polyethylene
Sclairfilm ® LWS-2-PA: medium density polyethylene
Hytrel ® 5556: polyester elastomer
B410: high density polyethylene
ELVAX ® 880: ethylene/vinyl acetate copolymer, 7.5 wt % vinyl acetate
Saran ® 18L: polyvinylidene chloride The results are summarized in Table 1.

TABLE 1

| Membrane | Thickness ($\mu$m) | Nicotine Flux ($\mu$g/cm² · h) | Nicotine Permeability ($\mu$g · 100 $\mu$m/cm² · h) |
|---|---|---|---|
| Dartek F101 | 78 | 20 | 16 |
| Sclairfilm HD-2-PA | 22 | 60 | 27 |
| Sclairfilm LWS-2-PA | 50 | 45 | 22 |
| Hytrel 5556 | 250 | 10 | 25 |
| B410 | 50 | 20 | 10 |
| ELVAX 880 | 100-150 | >200 | >200 |
| Saran 18L | 50 | 16 | 8 |

Test conditions: 30° C., released into saline from 3.9-cm² test devices

EXAMPLE 7-11

Reservoir embodiments

EXAMPLE 7

Figure 6:
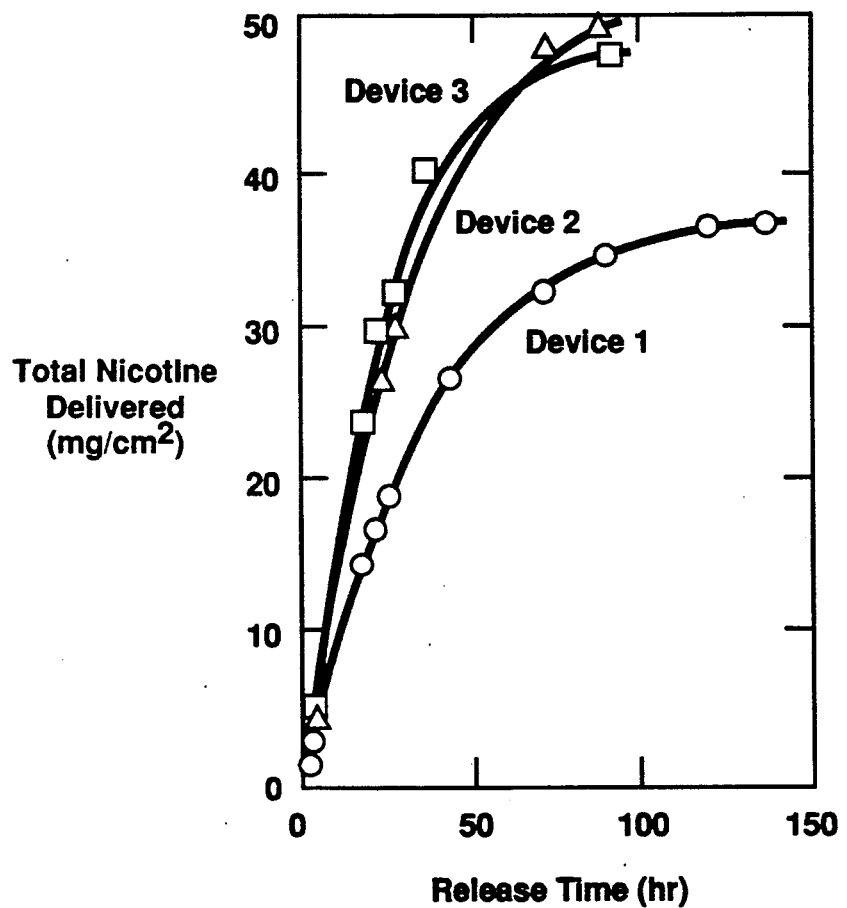
FIG. 6 is a graph of nicotine delivery through 100-micron thick Elvax 880 membranes, from a patch containing 200 $\mu$L pure nicotine, with a membrane area of 4.5 cm$^2$.

Experimental patches were made by heat sealing a backing of Scotch ® 1006 composite polyester tape to a 100-$\mu$m thick film of Elvax 880. The resulting pouches were filled with approximately 200 $\mu$L of nicotine, and the injection hole covered with a plug of hot melt glue. The finished characteristics of the patches were tested by the procedure described in Example 1, and the nicotine was released into saline at 37° C. The results are given for three individual patches in FIG. 6. The patches exhibited very high initial fluxes of the order 2 mg/cm².h. Half the nicotine load was delivered within the first 15-20 hours.

EXAMPLE 8

Figure 7:
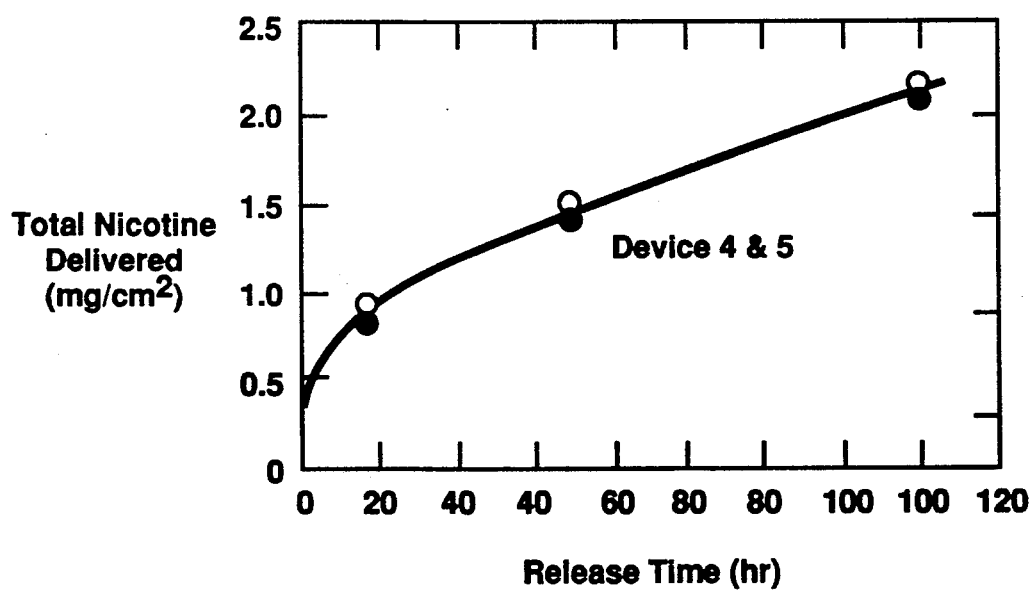
FIG. 7 is a graph of nicotine delivery through 100-micron thick Elvax 88 membranes, from a patch containing 200 $\mu$L of a 5% suspension of nicotine in a 20 wt % sodium sulfate solution, with a membrane area of 4.5 cm$^2$.

The patch-making procedure and release tests described in Example 7 were repeated using the same membrane, but with a load of 200 $\mu$L of 20 wt % sodium sulfate solution containing a 5% suspension of nicotine. The results are shown in FIG. 7. The patches exhibited a very high initial drug burst, followed by an average flux of about 8.5 $\mu$g/cm².h for the rest of the test period.

EXAMPLE 9

Figure 8:
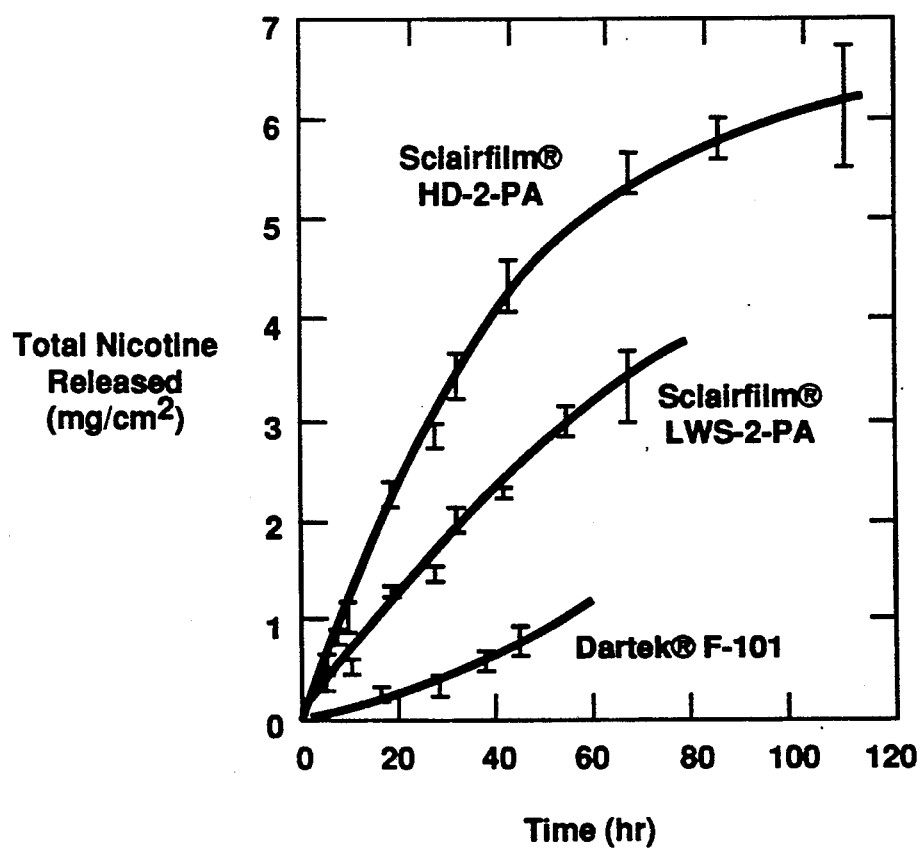
FIG. 8 is a graph of nicotine delivery from patches with nylon or polyethylene membranes. The nicotine content is 20-25 mg, and the patch area is 3.9 cm$^2$.

Experimental patches containing a disc of microporous nylon were made. A disc having an area of 3.9 cm² was punched from a sheet of microporous nylon 6,6. The disc was glued to a nonporous 78-$\mu$m thick film of Dartek F101. The disc was wetted with nicotine. The disc could hold about 20-25 $\mu$L of nicotine. The membrane/disc assembly was heated sealed to a backing of Scotch 1006 or 1220 composite polyester tape. The finished patches had an effective membrane area of 3.9 cm². The release characteristics of the patches were tested by the procedure described in Example 1. The results of the release tests are given as the lowest curve in FIG. 8. The flux from these patches was about 10 μg/cm$^2$.h during the first 10 or 15 hours, rising to about 20 μg/cm$^2$.h after about 20-25 hours.

EXAMPLE 10

The patch-making procedure and release tests described in Example 9 were repeated with a 22-μm thick film of Sclairfilm HD-2-PA as the membrane. The results are given as the upper curve in FIG. 8. The flux from the patch remained roughly constant at about 80 μg/cm$^2$.h for the first 60 hours, falling to about 30 μg/cm$^2$.h thereafter.

EXAMPLE 11

The patch-making procedure and release tests described in Example 9 were repeated with a 50-μm thick film of Sclairfilm LWS-2-PA as the membrane. The results are given as the middle curve in FIG. 8. The flux from the patch remained roughly constant at about 45-50 μg/cm$^2$.h.

EXAMPLES 12-17

Mixed Monolith/Membrane Systems

Monoliths containing 50% nicotine were made by the same general procedure as described in Example 1. For Example 12, a membrane of 100-μm thick Sclairfilm HD-2-PA was cast onto the monolith. For Example 13, a 38-μm thick membrane of polyethylene grade HD-106 obtained from Consolidated Thermplastics was cast onto the monolith. For Examples 14 and 15, the membranes of Examples 12 and 13 were coated with a 25-μm thick layer of BIO PSA grade X7-2920. For Example 16, the monolith was coated with polyethylene, double-sided, medical adhesive tape grade 3M-1509. For Example 17, the monolith was coated with polyethylene, double-sided, medical adhesive tape grade 3M-1512.

Figure 9:
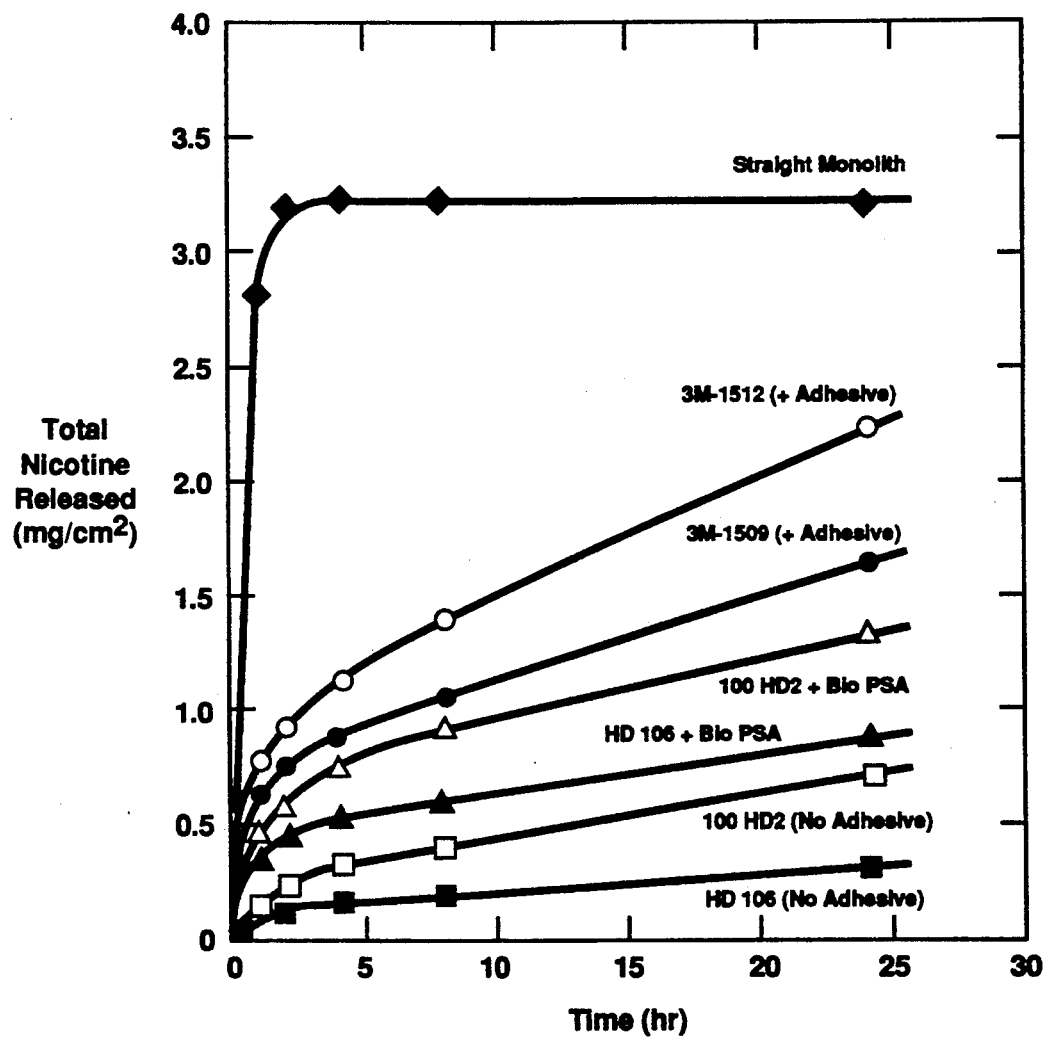
FIG. 9 is a graph of nicotine delivery from mixed monolith/membrane patches containing a 50% nicotine load, using a polyethylene membrane or a polyethylene medical tape.

Release tests were carried out as with the previous examples. The results for the various examples are given in FIG. 9. The upper curve shows the nicotine release from the monolith loaded with 50% nicotine without any membrane or adhesive. As can be seen, the presence of the membrane or membrane tape brings the steady-state flux down to 50 μg/cm$^2$.h or less.

EXAMPLES 18-21

Figure 10:
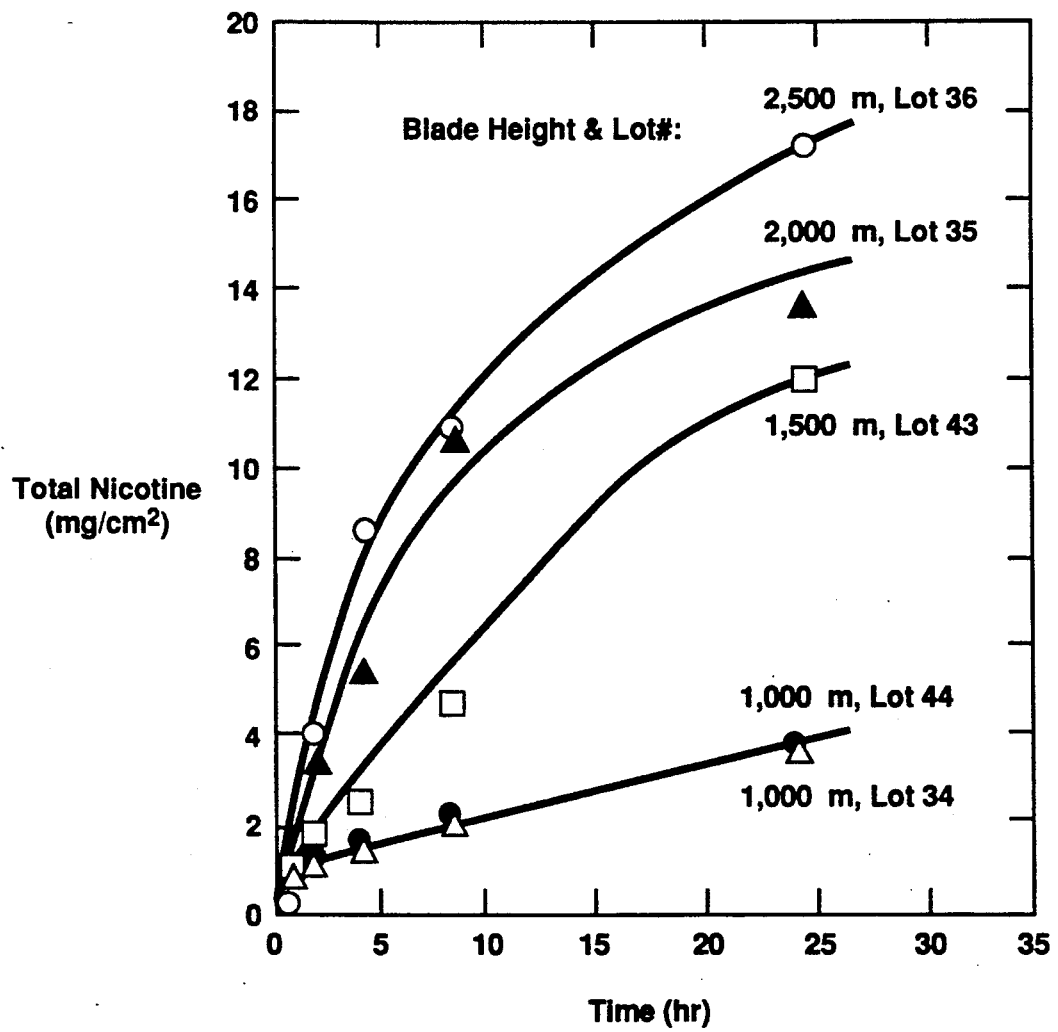
FIG. 10 is a graph of nicotine delivery from mixed monolith/membrane patches containing a 40% nicotine load, using a polyethylene membrane or a polyethylene medical tape.

Monoliths containing 40% nicotine were made by the same general procedure as described in Example 1. For Example 18, the monolith was cast with the blade height set at 1,000 μm. For Example 19, the monolith was cast with the blade height set at 1,500 μm. For Example 20, the monolith was cast with the blade height set at 2,000 μm. For Example 21, the monolith was cast with the blade height set at 2,500 μm. All monoliths were covered with 3M-1512 medical tape. Release tests were carried out as for the previous examples. The results are given in FIG. 10. A more pronounced burst effect was observed with the thicker monoliths, containing more nicotine. The 1,500 μm cast monolith maintained an average flux of about 500 μg/cm$^2$.h for 24 hours, and released a total of about 4 mg/cm$^2$ in the first 5 hours. The 1,000 μm cast monolith maintained an average flux of about 120 μg/cm$^2$.h for 24 hours, and released a total of about 1.5 mg/cm$^2$ in the first 5 hours.

EXAMPLES 22-25

Monoliths containing varying loads of nicotine were made as follows. A solution of nicotine-loaded Pellethane 2363-80AE was made by mixing Pellethane tablets and 12 wt % nicotine into tetrahydrofuran in a sealed mixing vessel. The solution was stirred for four hours. The backing material grade 3M #1109 was then coated on a knife over roll coater, and the solvent was driven off in three successive ovens at 24° C., 35° C., and 36° C., respectively. The cast film was then laminated to 3M MSX 100/75, which is a double-sided adhesive that consists of an adhesive layer, a polyethylene membrane, a second adhesive layer, and a release liner.

For Example 22, the monolith contained 37 mg of nicotine, with a patch area of 5 cm$^2$. For Example 23, the monolith contained 74 mg of nicotine, with a patch area of 10 cm$^2$. For Example 24, the monolith contained 60 mg of nicotine, with a patch area of 20 cm$^2$. For Example 25, the monolith contained 54 mg of nicotine, with a patch area of 30 cm$^2$.

Figure 11:
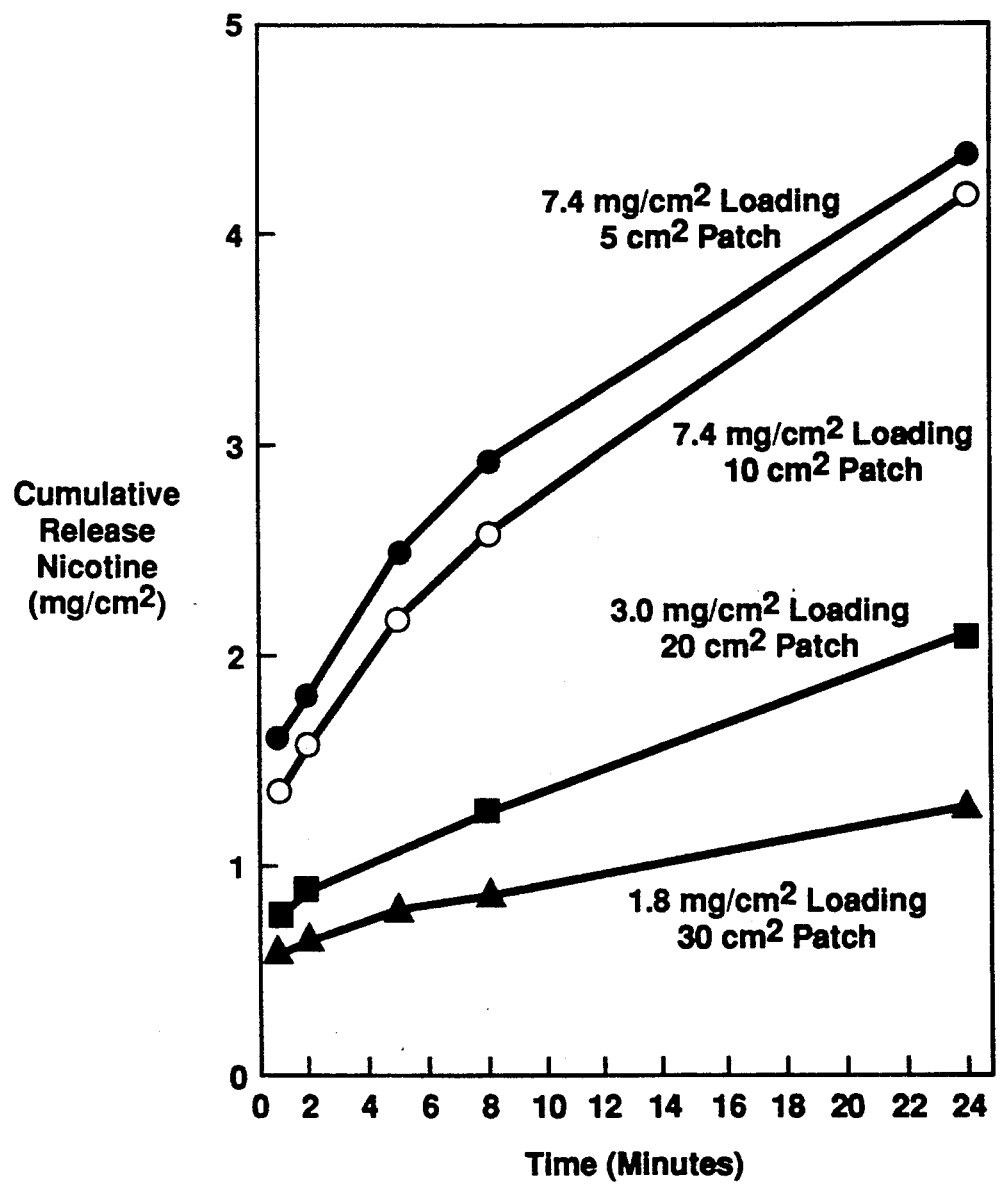
FIG. 11 is a graph of nicotine delivery from mixed monolith/membrane patches of various nicotine loads and sizes, using a double-sided adhesive that contains a polyethylene membrane.

Device release rate measurements were made as follows. Each transdermal system was attached to the disk assembly, adhesive side up, of a USP Dissolution Bath, as described in *The U.S. Pharmacopeia XXII, The National Formulary XVII*; U.S. Pharmacopeial Convention, Inc.: Rockville, MD, 1989; pp 1578-1583, herein incorporated by reference. The disk assembly was placed inside the dissolution vessel, which contained 500 mL of degassed, deionized water maintained at a constant temperature of 32°±0.5° C. The paddle was operated at a constant rate of 50 rpm at 25±2 mm from the surface of the disk assembly. Periodic samples were taken for HPLC analysis using a Dionex PCX-500 reverse-phase/ion exchange column. The results are given in FIG. 11. As shown, nicotine release per unit area is very similar for Examples 22 and 23, which have identical nicotine loadings of 7.4 mg/cm$^2$. For Examples 24 and 25, nicotine release per unit area declines as nicotine loadings of the patches decline.

EXAMPLES 26-28

Figure 12:
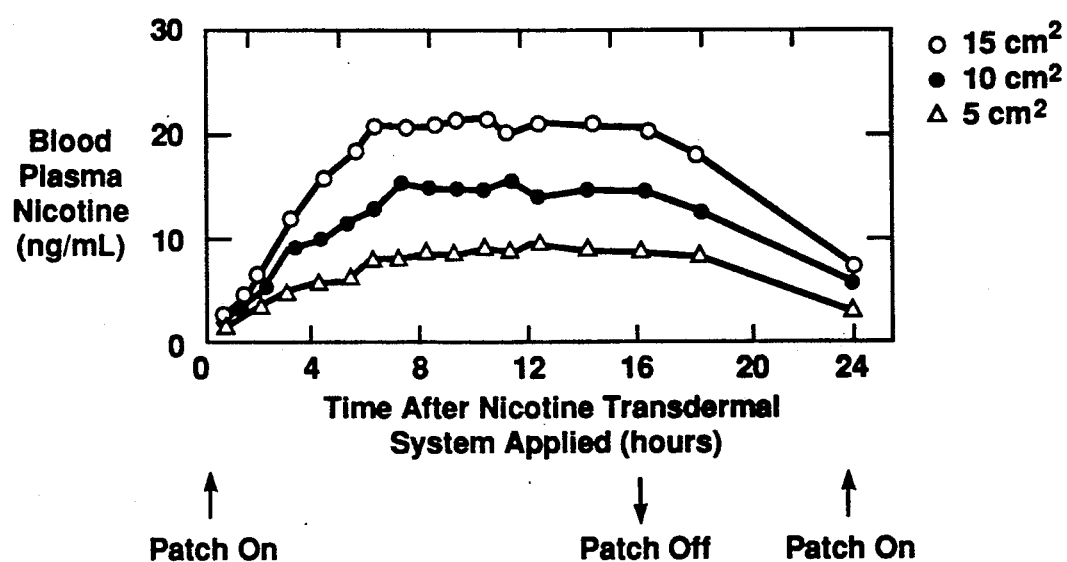
FIG. 12 is a graph of nicotine plasma levels after application of a transdermal nicotine systems with varying application areas.

The blood levels shown in FIG. 12 were obtained from 6 adult male smokers who had already developed a strong tolerance to nicotine. For all examples, transdermal nicotine systems used were manufactured as described in Examples 22-25, and each contained a total of 37 mg nicotine in a patch with an area of 5 cm$^2$, as in Example 22. For Example 26, a single 5 cm$^2$ transdermal nicotine patch was applied to the right forearm of each subject, and the patch remained affixed to the forearm for 16 hours. The lowest curve presents the average nicotine plasma level obtained. For Example 27, two 5 cm$^2$ transdermal nicotine patches were applied to the right forearm of each subject, and the patches remained affixed to the forearm for 16 hours. The middle curve presents the average nicotine plasma levels obtained. For Example 28, three 5 cm$^2$ transdermal nicotine patches were applied to the right forearm of each subject, and the patches remained affixed for 16 hours. The top curve presents the average nicotine plasma levels obtained. These test subjects were able to tolerate as many as 3×5 cm$^2$ patches with a total in vitro delivery of almost 70 mg/24 h without any untoward symptoms.

EXAMPLE 29

Nicotine Lozenge

FORMULATION

|  | Per tablet | Per kg | % |
| --- | --- | --- | --- |
| Nicotine free base | 2 mg | 1.25 g | 0.125 |
| Microcrystalline cellulose (a) | 100 mg | 62.50 g | 6.250 |
| Talc | 56 mg | 35.00 g | 3.500 |
| Magnesium stearate | 20 mg | 12.50 g | 1.250 |
| Mint flavor (b) | 15 mg | 9.37 g | 0.937 |
| Ammonium glycyrrhizinate (c) | 15 mg | 9.37 g | 0.937 |
| Dextrates (d) | 1392 mg | 870.00 g | 87.000 |

(a) = Avicel PH 101 ®
(b) = Pulvaromas mint
(c) = Glycamil ®
(d) = Emdex ®

MANUFACTURING METHOD—Direct compression

Equipment

Mortar
Turbula mixer
Sieve of 50 mesh
Single punch tablet press

Procedure

1. The first step was to adsorb the drug onto a carrier: for this purpose Avicel PH 101 was used. Nicotine was carefully mixed in a mortar with half the quantity of Avicel PH 101 required. When a good dispersion was obtained, the remaining quantity of Avicel PH 101 was added and incorporated.
2. Using a Turbula mixer, the dispersion obtained in Step 1 was mixed with talc, magnesium stearate, Pulvaromas mint, and Glycamil. The mixing must last at least 15 min. in order to obtain a homogenous blend.
3. In order to eliminate clumps, Emdex was sieved through a 50 mesh (300 micron) sieve. Emdex was then added to the blend of powders. To obtain the most homogeneous dispersion, Emdex was added in three separate steps.
4. 100 g of Emdex was added to the blend of powders and, using a Turbula mixer, mixed for at least 15 min.
5. Another 300 g of Emdex were added and mixed for at least 15 min.
6. The remaining quantity of Emdex was added and mixed for at least 15 min.
7. The powder was then compressed with a single punch press. A 16×16 mm punch was used to obtain lozenges with weight of 1.6 g and hardness of 15-20 Kp.

ADVANTAGES

1. Simple manufacturing method (no granulation required).
2. No heating required (nicotine is very volatile).

EXAMPLE 30

Buffered Nicotine Lozenge

FORMULATION

|  | Per tablet | Per kg | % |
| --- | --- | --- | --- |
| Nicotine free base | 2 mg | 1.25 g | 0.121 |
| Microcrystalline cellulose (a) | 100 mg | 62.50 g | 6.068 |
| Talc | 56 mg | 35.00 g | 3.398 |
| Magnesium stearate | 20 mg | 12.50 g | 1.213 |
| Mint flavor (b) | 15 mg | 9.37 g | 0.910 |
| Ammonium glycyrrhizinate (c) | 15 mg | 9.37 g | 0.910 |
| Dextrates (d) | 1392 mg | 870.00 g | 84.446 |
| Sodium carbonate | 32 mg | 20.00 g | 1.941 |
| Sodium hydroxycarbonate | 16 mg | 10.00 g | 0.971 |

(a) = Avicel PH 101 ®
(b) = Pulvaromas mint
(c) = Glycamil ®
(d) = Emdex ®

MANUFACTURING METHOD—Direct compression

Equipment

Mortar
Turbula mixer
Sieve of 50 mesh
Single punch tablet press

Procedure

1. The first step was to adsorb the drug onto a carrier: for this purpose Avicel PH 101 was used. Nicotine was carefully mixed in a mortar with half the quantity of Avicel PH 101 required. When a good dispersion was obtained, the remaining quantity of Avicel PH 101 was added and incorporated.
2. Using a Turbula mixer, the dispersion obtained in Step 1 was mixed with talc, magnesium stearate, Pulvaromas mint, Glycamil, sodium carbonate, and sodium hydroxycarbonate. The mixing must last at least 15 min. in order to obtain a homogenous blend.
3. In order to eliminate clumps, Emdex was sieved through a 50 mesh (300 micron) sieve. Emdex was then added to the blend of powders. To obtain the most homogeneous dispersion, Emdex was added in three separate steps.
4. 100 g of Emdex was added to the blend of powders and, using a Turbula mixer, mixed for at least 15 min.
5. Another 300 g of Emdex was added and mixed for at least 15 min.
6. The remaining quantity of Emdex was added and mixed for at least 15 min.
7. The powder was then compressed with a single punch press. A 16×16 mm punch was used to obtain lozenges with weight of 1.648 g and hardness of 15-20 Kp.

ADVANTAGES

1. Simple manufacturing method (no granulation required).
2. No heating required (nicotine is very volatile).

EXAMPLE 31

BUFFERED NICOTINE LOZENGE

FORMULATION

|  | Per tablet | Per kg | % |
| --- | --- | --- | --- |
| Nicotine free base | 2 mg | 1.25 g | 0.121 |
| Colloidal silica (a) | 10 mg | 6.06 g | 0.606 |
| Talc | 60 mg | 36.36 g | 3.636 |
| Magnesium stearate | 30 mg | 18.18 g | 1.818 |
| Lemon flavor (b) | 20 mg | 12.12 g | 1.212 |
| Mannitol | 200 mg | 121.21 g | 12.121 |
| Compressible sugar (c) | 1278 mg | 774.54 g | 77.454 |
| Sodium dihydrogen phosphate | 5 mg | 3.03 g | 0.303 |

-continued

| | Per tablet | Per kg | % |
|---|---|---|---|
| Disodium hydrogen phosphate | 45 mg | 27.27 g | 2.727 |

(a) = Aerosil 200 ®
(b) = Lemon flavor K4 S. Giorgio Essenze
(c) = Dipac ®

MANUFACTURING METHOD—Direct compression

Equipment

Mortar
Turbula mixer
Sieve of 50 mesh
Single punch tablet press

Procedure

1. Nicotine is adsorbed onto Aerosil 200, mixing very carefully. (Aerosil 200 acts as a carrier.) Nicotine is mixed in a mortar with half the quantity of Aerosil 200 required. When a good dispersion has been obtained, the remaining quantity is added and well mixed until a homogeneous dispersion is achieved.
2. Using a Turbula mixer, the dispersion of nicotine onto Aerosil 200 is then diluted with talc, magnesium stearate, lemon flavor K4, sodium dihydrogen phosphate, and disodium hydrogen phosphate. To obtain a homogeneous blend, the mixing must last at least 15 min.
3. Mannitol and Dipac are sieved together through a 50 mesh sieve to eliminate clumps.
4. The blend of the two sieved sugars is divided into three portions. Each part is added to the powders in the Turbula mixer and mixed for at least 15 min.
5. When the last portion has been added, the powder is compressed using a single punch press. A 16×16 mm punch is used to obtain lozenges with a weight of 1.650 g and hardness of 15 Kp.

ADVANTAGES

1. No heating required.
2. Simple manufacturing method.

EXAMPLE 32

BUFFERED NICOTINE LOZENGE

FORMULATION

| | Per tablet | Per kg | % |
|---|---|---|---|
| Nicotine free base | 2.0 mg | 6.93 g | 0.193 |
| Microcrystalline cellulose (a) | 60.0 mg | 58.03 g | 5.803 |
| Magnesium stearate | 15.0 mg | 14.51 g | 1.451 |
| Collidal silica (b) | 3.0 mg | 2.90 g | 0.290 |
| Gum arabic | 100.0 mg | 96.71 g | 9.671 |
| Starch | 200.0 mg | 193.42 g | 19.342 |
| Dextrates (c) | 600.0 mg | 580.27 g | 58.027 |
| Disodium hydrogen phosphate | 26.6 mg | 25.67 g | 2.567 |
| Citric acid | 0.8 mg | 0.77 g | 0.077 |
| Mint flavor (d) | 12.0 mg | 11.60 g | 1.160 |
| Ammonium glycyrrhizinate (e) | 12.0 mg | 11.60 g | 1.160 |

(a) = Avicel PH 101 ®
(b) = Aerosil 200 ®
(c) = Emdex ®
(d) = Pulvaromas mint
(e) = Glycamil ®

MANUFACTURING METHOD—Direct compression

Equipment

Mortar
Turbula mixer
Sieve 50 mesh
Single punch tablet press

Procedure

1. Avicel PH 101 and Aerosil 200 were well mixed in a Turbula mixer for at least 10 minutes.
2. Nicotine was adsorbed onto the blend obtained in Step 1, which acts as a carrier. This was accomplished by very carefully mixing nicotine in a mortar with half the quantity of the blend. When a good dispersion was obtained, the remaining quantity of the blend was added and mixed well until a homogeneous dispersion was achieved.
3. Magnesium stearate, gum arabic, starch, disodium hydrogen phosphate, citric acid, Pulvaromas mint, and Glycamil were added and mixed with the Turbula mixer for at least 15 min.
4. In order to eliminate clumps, Emdex was sieved through a 50 mesh (300 microns) sieve.
5. Emdex was then added to the blend of powders. To obtain the most homogeneous dispersion, Emdex was added in three separate steps, as described below. One hundred grams of Emdex were added to the blend of powders and, using a Turbula mixer, mixed for at least 15 min.
6. Another 300 g of Emdex were added and mixed for at least 15 min.
7. The remaining quantity of Emdex was added and mixed for at least 15 min.
8. The powder was then compressed with a single punch tablet. A 12×12 mm punch was used to obtain lozenges with a weight of 1.034 g and hardness of 15–20 Kp.

ADVANTAGES

1. Simple manufacturing method.
2. No heating required.

EXAMPLE 33

Buffered Nicotine Lozenge

FORMULATION

| | Per tablet | Per Kg | % |
|---|---|---|---|
| Nicotine free base | 2.00 mg | 2.79 g | 0.279 |
| Talc | 20.00 mg | 27.98 g | 2.798 |
| Colloidal silica (a) | 10.00 mg | 13.99 g | 1.399 |
| Lactose | 400.00 mg | 559.67 g | 55.967 |
| Glycerin | 2.00 mg | 2.80 g | 0.280 |
| Cocoa powder | 200.00 mg | 279.84 g | 27.984 |
| Gelatin (sol. 4%) | 60.00 mg | 83.95 g | 8.395 |
| Tri hydroxymethylaminomethane | 20.70 mg | 28.87 g | 2.887 |

(a) = Aerosil 200 ®

MANUFACTURING METHOD—Granulation

Equipment

Mortar
Tonazzi kneading machine
Buhler oven
Alexanderwerk granulator
Turbula mixer Single punch tablet press Procedure 1. Nicotine is adsorbed onto Aerosil 200, which acts as a carrier. This is accomplished by very carefully mixing nicotine in a mortar with half the quantity of Aerosil 200 required. When a good dispersion is obtained, the remaining quantity is added and mixed well until a homogeneous dispersion is achieved.
2. In a Tonazzi kneading machine, lactose is mixed with cocoa powder, talc, and trihydroxymethylaminomethane. The blend of powder is then kneaded using glycerin and the gelatin solution as granulating liquids.
3. The mixture obtained is granulated using an Alexanderwerk granulator equipped with a No. 2 screen.
4. The granulate obtained is dried in a Buhler oven with circulating air at 50° C. up to a moisture content of 3%.
5. The granulate is mixed using a Turbula mixer with the dispersion of nicotine on Aerosil 200.
6. The powder is then compressed with a single punch press. An 11×11 mm punch is used to obtain lozenges with a weight of 714.7 mg and hardness of 15–20 Kp.

ADVANTAGES

1. Using cocoa powder, no flavoring agents are required.
2. The granulate does not contain nicotine, which is added to the formulation in dry form after dispersion onto Aerosil 200.

EXAMPLE 34

Buffered Nicotine Lozenge

FORMULATION

|  | Per tablet | Per Kg | % |
|---|---|---|---|
| Nicotine free base | 2.00 mg | 1.73 g | 0.173 |
| Microcrystalline cellulose (a) | 100.00 mg | 86.46 g | 8.646 |
| Talc | 5.00 mg | 4.32 g | 0.432 |
| Polyvinylpyrrolidone | 114.00 mg | 98.56 g | 9.856 |
| Carboxymethylcellulose | 28.00 mg | 24.21 g | 2.421 |
| Sucrose | 850.00 mg | 734.91 g | 73.491 |
| Magnesium carbonate | 12.00 mg | 10.38 g | 1.038 |
| Mint flavor (b) | 12.00 mg | 10.37 g | 1.037 |
| Ammonium glycyrrhizinate (c) | 12.00 mg | 10.37 g | 1.037 |

(a) = Avicel PH 101 ®
(b) = Pulvaromas mint ®
(c) = Glycamil ®

MANUFACTURING METHOD—Granulation

Equipment

Mortar
Tonazzi kneading machine
Buhler oven
Alexanderwerk granulator
Turbula mixer
Single punch tablet press Procedure 1. Nicotine was adsorbed onto Avicel PH 101, which acts as a carrier. This was accomplished by very carefully mixing nicotine in a mortar with half the quantity of Avicel PH 101 required. When a good dispersion was obtained, the remaining quantity was added and mixed well until a homogeneous dispersion was achieved.
2. In a Tonazzi kneading machine, sucrose, magnesium carbonate, and talc were kneaded using carboxymethylcellulose (5% aqueous solution) and polyvinylpyrrolidone (5% alcoholic solution) as granulating liquids. The mixture obtained was then granulated using an Alexanderwerk granulator equipped with a No. 2 screen and dried in a Buhler oven with circulating air at 50° C. up to a moisture content of 3%.
3. The granulate obtained was mixed, in a Turbula mixer, with the dispersion of nicotine onto Avicel PH 101, Pulvaromas mint, and Glycamil for at least 15 min.
4. The blend of powders is compressed using a single punch press. A 16×16 mm punch is used to obtain lozenges with a weight of 1.156 g and hardness of 15 Kp.

ADVANTAGES

1. The granulate does not contain nicotine, which is added to the formulation in dry form after dispersion onto Avicel PH 101.

EXAMPLE 35

Buffered Nicotine Lozenge

FORMULATION

|  | Per tablet | Per Kg | % |
|---|---|---|---|
| Nicotine free base | 2.00 mg | 2.47 g | 0.247 |
| Microcrystalline cellulose (a) | 100.00 mg | 123.52 g | 12.352 |
| Talc | 20.00 mg | 24.70 g | 2.470 |
| Magnesium stearate | 5.00 mg | 6.18 g | 0.618 |
| Gum arabic | 7.00 mg | 8.65 g | 0.865 |
| Starch | 25.0 mg | 30.88 g | 3.088 |
| Tragacanth | 3.00 mg | 3.70 g | 0.370 |
| Sucrose | 600.00 mg | 741.11 g | 74.111 |
| Disodium hydrogen phosphate | 22.80 mg | 28.16 g | 2.816 |
| Citric acid | 0.80 mg | 0.99 g | 0.099 |
| Mint flavor (b) | 12.00 mg | 14.82 g | 1.482 |
| Ammonium glycyrrhizinate (c) | 12.00 mg | 14.82 g | 1.482 |

(a) = Avicel PH 101 ®
(b) = Pulvaromas mint ®
(c) = Glycamil ®

MANUFACTURING METHOD

Equipment

Mortar
Tonazzi kneading machine
Buhler oven
Alexanderwerk granulator
Turbula mixer
Single punch tablet press Procedure 1. Nicotine is adsorbed onto Avicel PH 101, which acts as a carrier. This is accomplished by very carefully mixing nicotine in a mortar with half the quantity of Avicel PH 101 required. When a good dispersion is obtained, the remaining quantity is added and mixed well until a homogeneous dispersion is achieved.
2. Talc, starch, tragacanth, sucrose, disodium hydrogen phosphate, and citric acid are kneaded in a Tonazzi kneading machine using gum arabic dispersed in water as granulating liquid.
3. The mixture obtained in Step 2. is granulated using an Alexanderwerk granulator equipped with a No. 2 screen and dried in a Buhler oven with circulating air at 50° C. up to a moisture content of 3%.

4. The granulate obtained in Step 3. is mixed in a Turbula mixer with the dispersion of nicotine onto Avicel PH 101, magnesium stearate, Pulvaromas mint, and Glycamil for at least 15 min.
5. The blend of powders is compressed using a single punch tablet press. An 11×11 mm punch is used to obtain lozenges with a weight of 809.6 g and hardness of 15 Kp.

ADVANTAGES

1. The granulate does not contain nicotine, which is added to the formulation in dry form after dispersion onto Avicel PH 101.

EXAMPLE 36

Buffered Nicotine Lozenge

FORMULATION

|  | Per tablet | Per Kg | % |
| --- | --- | --- | --- |
| Nicotine free base | 2.00 mg | 2.16 g | 0.216 |
| Microcrystalline cellulose (a) | 35.00 mg | 37.83 g | 3.783 |
| Talc | 35.00 mg | 37.83 g | 3.383 |
| Gum arabic | 18.0 mg | 19.45 g | 1.945 |
| Stearic acid | 1.20 mg | 1.29 g | 0.129 |
| Mannitol | 800.00 mg | 864.58 g | 86.068 |
| Mint flavor (b) | 12.00 mg | 12.97 g | 1.097 |
| Ammonium glycyrrhizinate (c) | 12.00 mg | 12.97 g | 1.097 |
| Sodium carbonate | 20.00 mg | 21.60 g | 2.160 |
| Sodium hydroxycarbonate | 10.00 mg | 10.80 g | 1.080 |

(a) = Avicel PH 101 ®
(b) = Pulvaromas mint ®
(c) = Glycamil ®

MANUFACTURING METHOD—Granulation

Equipment

Mortar
Tonazzi kneading machine
Buhler oven
Alexanderwerk granulator
Turbula mixer
Single punch tablet press Procedure 1. Nicotine is adsorbed onto Avicel PH 101, which acts as a carrier. This is accomplished by very carefully mixing nicotine in a mortar with half the quantity of Avicel PH 101 required. When a good dispersion is obtained, the remaining quantity is added and mixed well until a homogeneous dispersion is achieved.
2. In a Tonazzi kneading machine, mannitol is kneaded using an aqueous solution (10%) of gum arabic. The mixture obtained is granulated using an Alexanderwerk granulator equipped with a No. 2 screen, and then dried in a Buhler oven with circulating air at a temperature of 50° C. up to a moisture content of 3%.
3. Using a Turbula mixer, the granulate obtained in Step 2. is mixed with the dispersion of nicotine onto Avicel PH 101 for at least 15 min.
4. Then talc, stearic acid, mint flavor, Pulvaromas mint, Glycamil, sodium carbonate, and sodium hydroxycarbonate are added and mixed for at least 15 min.
5. The blend of powders is compressed using a single punch press. A 12×12 mm punch is used to obtain lozenges with a weight of 942.6 mg and hardness of 15 Kp.

ADVANTAGES

1. The granulate does not contain nicotine, which is added to the formulation in dry form after dispersion onto Avicel PH 101.

EXAMPLE 37

Buffered Nicotine Sublingual Tablet

FORMULATION

|  | Per tablet | Per kg | % |
| --- | --- | --- | --- |
| Nicotine free base | 2.0 mg | 5.83 g | 0.583 |
| Microcrystalline cellulose (a) | 50.0 mg | 145.69 g | 14.569 |
| Magnesium stearate | 2.6 mg | 7.57 g | 0.757 |
| Colloidal silica (b) | 5.0 mg | 14.57 g | 1.457 |
| Gum arabic | 4.0 mg | 11.65 g | 1.165 |
| Polyvinyl alcohol | 1.2 mg | 3.50 g | 0.350 |
| Starch | 53.0 mg | 154.43 g | 15.443 |
| Mannitol | 32.0 mg | 93.24 g | 9.324 |
| Lactose | 38.4 mg | 111.89 g | 11.189 |
| Sucrose | 137.0 mg | 399.18 g | 39.918 |
| Disodium hydrogen phosphate | 9.7 mg | 28.26 g | 2.826 |
| Citric acid | 0.3 mg | 0.87 g | 0.087 |
| Mint flavor (c) | 4.0 mg | 11.65 g | 1.165 |
| Ammonium glycyrrhizinate (d) | 4.0 mg | 11.65 g | 1.165 |

(a) = Avicel PH 101 ®
(b) = Aerosil 200 ®
(c) = Pulvaromas mint
(d) = Glycamil ®

MANUFACTURING METHOD—Granulation

Equipment

Mortar
Tonazzi kneading equipment
Alexanderwerk granulator
Buhler air circulating oven
Turbula mixer
Single punch tablet press Procedure 1. Avicel PH 101 and Aerosil 200 are well mixed in a Turbula mixer for at least 10 min.
2. Nicotine is adsorbed onto the blend obtained in Step 1., which acts as a carrier. This is accomplished by very carefully mixing nicotine in a mortar with half the quantity of the blend. When a good dispersion is obtained, the remaining quantity is added and mixed well until a homogeneous dispersion is achieved.
3. A granulate is then prepared by mixing in a Tonazzi kneading machine gum arabic, polyvinyl alcohol, mannitol, starch, disodium hydrogen phosphate, citric acid, lactose, and sucrose. Water is used as a granulating liquid.
4. The mixture obtained is then granulated using an Alexanderwerk granulator equipped with a No. 2 screen.
5. The granulate is dried in a Buhler oven with circulating air at 50° C. up to a moisture content of 3%.
6. Using a Turbula mixer, the dispersion of nicotine onto Avicel PH 101 and Aerosil 200 is mixed with the granulate obtained in Step 5. for at least 15 min.
7. Magnesium stearate, Pulvaromas mint, and Glycamil are added in the Turbula mixer and mixed with the blend obtained in Step 6. for at least 15 min.
8. The blend of powders is compressed using single punch tablet press equipped with a 9 mm diameter biconvex punch, obtaining tablets with a weight of 343.2 mg and hardness of 15 Kp.

ADVANTAGES

1. The granulate does not contain nicotine, which is added to the formulation in dry form after dispersion onto Avicel PH 101.

EXAMPLE 38

Buffered Nicotine Sublingual Capsule (Chewable Soft Gelatin Capsules)

FORMULATION

|  | Per tablet | Per Kg | % |
| --- | --- | --- | --- |
| Nicotine free base | 2.00 mg | 4.37 g | 0.437 |
| Glycerol | 20.40 mg | 44.58 g | 4.458 |
| Water | 34.00 mg | 74.30 g | 7.430 |
| Sodium saccharinate | 0.50 mg | 1.09 g | 0.109 |
| Polyethylene glycol (a) | 386.00 mg | 843.53 g | 84.353 |
| Mint flavor (b) | 0.70 mg | 1.53 g | 0.153 |
| Ammonium glycyrrhizinate (c) | 0.70 mg | 1.53 g | 0.153 |
| Disodium hydrogen phosphate | 12.90 mg | 28.19 g | 2.819 |
| Citric acid | 0.40 mg | 0.87 g | 0.087 |

(a) = Carbowax 400 ®
(b) = Pulvaromas mint
(c) = Glycamil

MANUFACTURING METHOD

Equipment

Stainless steel reactor
Stainless steel container
Scherer capsulation machine

Procedure

1. Glycerol, water, sodium saccharinate, and Carbowax 400 are mixed in a stainless steel reactor for at least 15 min.
2. Disodium hydrogen phosphate and citric acid are added and mixed for at least 10 min.
3. While stirring well, nicotine, Pulvaromas, and glycamil are added. The mixture is stirred for at least 15 min.
4. The mixture obtained in Step 2. is transferred to a stainless steel container.
5. The following shell constituents are introduced into a stainless steel container: gelatin, glycerin, titanium dioxide, sodium ethyl hydroxybenzoate, and sodium propyl hydroxybenzoate. (For a capsule content of 450 mg, typical quantities of shell constituents would be gelatin—140 mg, glycerin—67 mg, titanium dioxide—2.8 mg, sodium ethyl hydroxybenzoate—0.6 mg, and sodium propyl hydroxybenzoate—0.5 mg.) They are melted at 70° C. The mixture is stirred for 15 min. to make it homogeneous.
6. The Pulvaromas mint is added to the melted mixture for the shell and stirred for 2 min.
7. The Scherer capsulation machine is filled with the melted mixture obtained in Step 6.
8. The capsules are produced in the predetermined shape and volume, and the solution obtained in Step 3. is injected inside them by means of special nozzles.

ADVANTAGES

1. Precision of dosing.
2. It is possible to obtain a flavored soft gelatin capsule.

We claim:

1. A method of smoking cessation therapy comprising the concurrent transdermal and buccal administration of nicotine wherein said buccally administered nicotine provides transient blood levels of nicotine about 5 ng/ml above that provided by the transdermal administration of nicotine.

2. A method of smoking cessation therapy as described in claim 1, wherein said transdermal administration of nicotine from said transdermal system results in nicotine blood levels of between 5 to 30 ng/mL for at least 12 hours.

3. A method of smoking cessation therapy as described in claim 1, wherein said buccal nicotine administration results in maximum nicotine blood levels that are at least 5 ng/mL above the maximum nicotine blood level provided by said transdermal administration of nicotine.

4. A method of smoking cessation therapy as described in claim 1, wherein said buccal nicotine administration results in maximum nicotine blood levels from 2 to 30 minutes after said buccal nicotine administration.

5. A method of smoking cessation therapy as described in claim 1, wherein said buccal nicotine administration results in maximum nicotine blood levels from 2 to 10 minutes after said buccal nicotine administration.

6. A method of smoking cessation therapy as described in claim 1, wherein said buccal nicotine administration obtained by allowing a nicotine lozenge to completely dissolve in the mouth results in maximum nicotine blood levels from 2 to 10 minutes after said buccal nicotine administration.

7. A method of smoking cessation therapy as described in claim 1, wherein said buccal nicotine administration comprises nicotine lozenges formulated to a pH of between 7 and 11.

8. A method of smoking cessation therapy as described in claim 1, wherein said buccal nicotine administration comprises nicotine tablets formulated to a pH of between 7 and 11.

9. A method of smoking cessation therapy as described in claim 1, wherein said buccal nicotine administration comprises nicotine capsules formulated to a pH of between 7 and 11.

10. The method of smoking cessation therapy as described in claim 1, wherein said transdermal system comprises:
    (a) A nicotine depot layer, having a skin-facing side and a skin-distal side, said depot layer containing a sufficient quantity of nicotine to maintain a useful flux of nicotine from said patch for a total time period of 12 hours or more;
    (b) an occlusive backing layer in contact with and covering said depot layer on said skin-distal side; and
    (c) rate-controlling means for controlling diffusion of nicotine from said skin-facing side at a first flux of greater than zero but less than 2 mg/cm$^2$ in any hour for a first time period of greater than zero but less than 5 hours, then at a second flux between 20 and 800 $\mu$g/cm$^2$.h for a second time period of 7 hours or more.

11. A method of smoking cessation therapy as described in claim 9, wherein said transdermal administration of nicotine from a transdermal system or systems results in nicotine blood levels of between 5 to 30 ng/mL for at least 12 hours.

12. A method of smoking cessation therapy as described in claim 9, wherein said buccally administered nicotine result in maximum nicotine blood levels that are at least 5 ng/mL more than the maximum nicotine blood level provided by said transdermal administration of nicotine.

13. A method of smoking cessation therapy as described in claim 9, wherein said buccally administered nicotine in maximum nicotine blood levels from 2 to 30 minutes after said buccal nicotine administration.

14. A method of smoking cessation therapy as described in claim 9, wherein said nicotine lozenges, tablets, or capsules results in maximum nicotine blood levels from 2 to 10 minutes after said buccally administered nicotine.

15. A method of smoking cessation therapy as described in claim 9, wherein said nicotine lozenges, are formulated at a pH of between 7 and 11.

16. A method of smoking cessation therapy as described in claim 9, wherein said nicotine capsules are formulated at a pH of between 7 and 11.

17. A method of smoking cessation therapy as described in claim 9, wherein said nicotine tablets are formulated at a pH of between 7 and 11.

* * * * *

UNITED STATES PATENT AND TRADEMARK OFFICE
CERTIFICATE OF CORRECTION

PATENT NO. : 5,135,753
DATED : August 4, 1992
INVENTOR(S) : Baker, et al

Page 1 of 3

It is certified that error appears in the above-indentified patent and that said Letters Patent is hereby corrected as shown below:

In the Drawings, Fig. 3 should be deleted to appear as shown below:

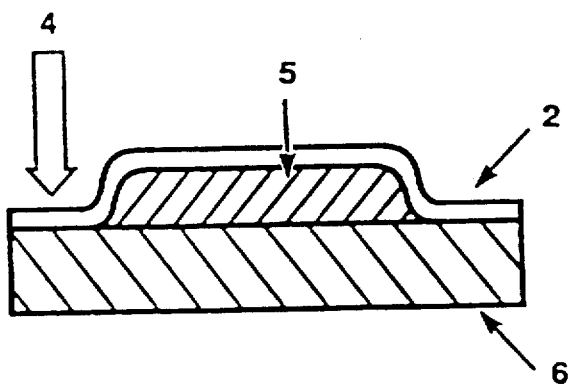

FIG. 3

UNITED STATES PATENT AND TRADEMARK OFFICE
CERTIFICATE OF CORRECTION

PATENT NO. : 5,135,753
DATED : August 4, 1992
INVENTOR(S) : Baker, et al.

It is certified that error appears in the above-indentified patent and that said Letters Patent is hereby corrected as shown below:

Column 4, line 12, "provides a initial" should read --provides an initial--;

Column 5, line 54, "the period use" should read --the periodic use--;

Column 6, line 39, "as the dissolve" should read --as they dissolve--;

Column 13, line 53, "permiabilities" should read --permeabilities--

Column 14, lines 16-17, "may be conveniently be attached" should read --may be conveniently attached--;

Column 18, line 63, "was heated sealed" should read --was heat sealed--

UNITED STATES PATENT AND TRADEMARK OFFICE
CERTIFICATE OF CORRECTION

PATENT NO. : 5,135,753
DATED : August 4, 1992
INVENTOR(S) : Baker, et al.

It is certified that error appears in the above-indentified patent and that said Letters Patent is hereby corrected as shown below:

Column 30, lines 61 and 66; Column 31, lines 5 and 10; and Column 32, lines 4, 7, and 10, each occurrence of "in claim 9" should —in claim 10—.

Signed and Sealed this

Twenty-ninth Day of March, 1994

*Attest:*

BRUCE LEHMAN

*Attesting Officer*     *Commissioner of Patents and Trademarks*